US012729191B2

(12) United States Patent
Nagai et al.

(10) Patent No.: US 12,729,191 B2
(45) Date of Patent: Sep. 8, 2026

(54) PRODUCTION METHOD FOR SYNTHETIC INTERMEDIATE OF MONOCYCLIC PYRIDINE DERIVATIVE

(71) Applicant: Eisai R&D Management Co., Ltd., Tokyo (JP)

(72) Inventors: Mitsuo Nagai, Kamisu (JP); Takashi Fukuyama, Tsukuba (JP); Yasuaki Kamada, Tokyo (JP); Jun Niijima, Tsukuba (JP); Hirofumi Kuroda, Kamisu (JP); Yuki Karoji, Kamisu (JP); Keiichi Murakami, Kamisu (JP); Masayuki Omori, Kamisu (JP); Yusuke Miyashita, Kamisu (JP); Atsushi Kamada, Tsukuba (JP); Masaaki Matsuda, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 367 days.

(21) Appl. No.: 18/292,731

(22) PCT Filed: Aug. 29, 2022

(86) PCT No.: PCT/JP2022/032309
§ 371 (c)(1),
(2) Date: Jan. 26, 2024

(87) PCT Pub. No.: WO2023/032872
PCT Pub. Date: Mar. 9, 2023

(65) Prior Publication Data

US 2024/0294496 A1 Sep. 5, 2024

(30) Foreign Application Priority Data

Aug. 31, 2021 (JP) ................................. 2021-141245

(51) Int. Cl.

| | |
|---|---|
| ***C07D 401/12*** | (2006.01) |
| ***C07C 201/12*** | (2006.01) |
| ***C07C 253/30*** | (2006.01) |
| ***C07D 209/08*** | (2006.01) |

(52) U.S. Cl.
CPC .......... *C07D 401/12* (2013.01); *C07C 201/12* (2013.01); *C07C 253/30* (2013.01); *C07D 209/08* (2013.01)

(58) Field of Classification Search
CPC .. C07D 401/12; C07D 209/08; C07C 201/12; C07C 253/30
USPC ...................................................... 546/278.1
See application file for complete search history.

(56) References Cited

U.S. PATENT DOCUMENTS

| | | | |
|---|---|---|---|
| 6,831,175 | B2 | 12/2004 | Li et al. |
| 7,109,219 | B2 | 9/2006 | Tsuruoka et al. |
| 7,253,286 | B2 | 8/2007 | Funahashi et al. |
| 8,131,527 | B1 | 3/2012 | Saxty et al. |
| 8,614,216 | B2 | 12/2013 | Okhamafe et al. |
| 8,933,099 | B2 | 1/2015 | Funahashi et al. |
| 9,951,047 | B2 | 4/2018 | Ozaki et al. |
| 11,219,619 | B2 | 1/2022 | Yamaguchi et al. |
| 2003/0232883 | A1 | 12/2003 | Jolidon et al. |
| 2004/0053908 | A1 | 3/2004 | Funahashi et al. |
| 2004/0122029 | A1 | 6/2004 | Liu et al. |
| 2004/0204427 | A1 | 10/2004 | Chen et al. |
| 2004/0210079 | A1 | 10/2004 | Jolidon et al. |
| 2005/0187236 | A1 | 8/2005 | Tsuruoka et al. |
| 2005/0256154 | A1 | 11/2005 | Luk et al. |
| 2005/0283019 | A1 | 12/2005 | Jolidon et al. |

(Continued)

FOREIGN PATENT DOCUMENTS

| | | |
|---|---|---|
| AU | 2014219811 | 8/2014 |
| CA | 2974937 | 9/2016 |

(Continued)

OTHER PUBLICATIONS

[No Author Listed], "Clinical guidelines for the diagnosis and treatment of patients with breast cancer," Approved at the Meeting of the Board of the Association of Oncologists of Russia, Moscow, 2014, pp. 1-43, 86 pages (with Machine Translation).

(Continued)

*Primary Examiner* — Kristin A Vajda
(74) *Attorney, Agent, or Firm* — Fish & Richardson P.C.

(57) ABSTRACT

The invention provides a production process allowing more high-yield and efficient synthesis of key intermediates (compound (2i) or a salt thereof, and compound (1g)) for production of E7090, which is useful as an FGFR inhibitor.

(1g)

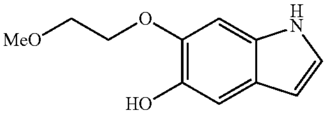

(2i)

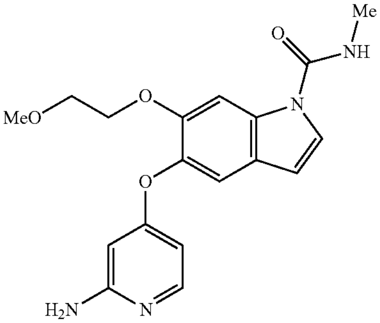

7 Claims, No Drawings

(56) References Cited

U.S. PATENT DOCUMENTS

2008/0108648 A1 5/2008 Alcouffe et al.
2011/0021493 A1 1/2011 Schirok et al.
2011/0060215 A1 3/2011 Tupin et al.
2012/0270918 A1 10/2012 Abecassis et al.
2013/0338134 A1 12/2013 Wu et al.
2014/0142084 A1 5/2014 Kameda et al.
2014/0148483 A1 5/2014 Semba et al.
2014/0155385 A1 6/2014 Barf et al.
2014/0235614 A1 8/2014 Funasaka et al.
2014/0378422 A1 12/2014 Yovine et al.
2015/0191791 A1 7/2015 Shibata
2017/0217935 A1 8/2017 Ozaki et al.
2018/0015079 A1 1/2018 Shibata et al.
2018/0065951 A1 3/2018 Buschmann et al.
2018/0303817 A1 10/2018 Miyano et al.
2019/0111043 A1 4/2019 Shibata et al.
2020/0277387 A1 9/2020 Currie
2020/0375970 A1 12/2020 Yamaguchi et al.
2023/0149381 A1 5/2023 Nishibata et al.
2023/0243813 A1 8/2023 Milburn et al.

FOREIGN PATENT DOCUMENTS

CA 3001969 6/2017
CA 3091153 10/2019
CL 201400130 8/2014
CN 1678607 10/2005
CN 101024627 8/2007
CN 103917545 7/2014
CN 106660997 5/2017
CN 107205996 9/2017
EP 1415987 5/2004
EP 1522540 4/2005
EP 2657233 8/2014
EP 2960238 A4 8/2016
EP 3275442 1/2018
JP 2005-527617 A 9/2005
JP 2008-533111 3/2006
JP 2006-522756 10/2006
JP 2009-108032 5/2009
JP 2009-523410 A 6/2009
JP 2009-215313 9/2009
JP 2010-539110 A 12/2010
JP 5600229 10/2014
JP 2014-237707 12/2014
JP 2015-505562 2/2015
JP 5925978 4/2016
JP 2017-206437 11/2017
JP 2018-507220 3/2018
JP 2018-512391 5/2018
JP 2018-538274 12/2018
JP 2023-500054 A 1/2023
KR 10-2005-0059151 6/2005
KR 10-2017-0035927 3/2017
KR 102050128 11/2019
RU 2257380 7/2005
RU 2005108999 8/2005
RU 2345077 2/2006
RU 2310651 11/2007
RU 2645352 8/2018
RU 2712222 C2 1/2020
TW 200413353 8/2004
WO WO 2002/032872 4/2002
WO WO 2004/002410 1/2004
WO WO 2004/020434 3/2004
WO WO 2006/000420 1/2006
WO WO 2006/097625 9/2006
WO WO 2007/067968 A2 6/2007
WO WO 2007/071752 6/2007
WO WO 2008/008747 1/2008
WO WO 2008/012690 1/2008
WO WO 2008/075068 6/2008
WO WO 2008/078091 7/2008
WO WO 2008/078100 7/2008
WO WO 2009/001070 12/2008
WO WO 2009/019518 2/2009
WO WO 2009/047506 4/2009
WO WO 2009/047522 4/2009
WO WO 2009/056886 5/2009
WO WO 2009/076602 6/2009
WO WO 2009/117421 9/2009
WO WO 2009/141386 11/2009
WO WO 2009/150240 12/2009
WO WO 2009/153592 12/2009
WO WO 2010/078421 7/2010
WO WO 2010/078427 7/2010
WO WO 2010/078430 7/2010
WO WO 2010/119284 10/2010
WO WO 2010/119285 10/2010
WO WO 2011/001122 1/2011
WO WO 2011/001413 1/2011
WO WO 2011/016528 2/2011
WO WO 2011/051425 5/2011
WO WO 2011/071821 6/2011
WO WO 2011/135376 11/2011
WO WO 2012/004732 1/2012
WO WO 2012/073017 6/2012
WO WO 2012/088266 6/2012
WO WO 2012/157672 A1 11/2012
WO WO 2013/010380 1/2013
WO WO 2013/061074 5/2013
WO WO 2013/061077 5/2013
WO WO 2013/061080 5/2013
WO WO 2013/061081 5/2013
WO WO 2013/087744 6/2013
WO WO 2013/108809 7/2013
WO WO 2013/116293 8/2013
WO WO 2013/129369 9/2013
WO WO 2013/151913 10/2013
WO WO 2013/179034 12/2013
WO WO 2014/007369 1/2014
WO WO 2014/011900 1/2014
WO WO 2014/026125 2/2014
WO WO 2014/044846 3/2014
WO WO 2014/048878 3/2014
WO WO 2014/051022 3/2014
WO WO 2014/129477 8/2014
WO WO 2014/145751 9/2014
WO WO 2014/162039 10/2014
WO WO 2016/027780 A1 2/2016
WO WO 2016/027781 2/2016
WO WO 2016/084883 6/2016
WO WO 2016/134234 8/2016
WO WO 2016/141218 9/2016
WO WO 2016/152907 9/2016
WO WO 2017/091577 6/2017
WO WO 2017/104739 6/2017
WO WO 2018/049233 3/2018
WO WO 2019/189241 10/2019
WO WO 2020/014440 1/2020
WO WO 2021/092071 A1 5/2021
WO WO 2021/210636 10/2021
WO WO 2023/130072 A1 7/2023

OTHER PUBLICATIONS

Kholodov et al., "Clinical Pharmacokinetics," Moscow, "Medicine," 1985, Chapter 3, pp. 83-98, 134-138, 160, and 378-380, 52 pages (with English Translation).
Meshcheryakov et al., "Fulvestrant—endocrine therapy with an extended spectrum of action," Modern Oncology, 2012, 3(14):37-40, 7 pages (with English Translation).
Office Action in Chinese Patent Application No. 202180045666.7, dated Apr. 1, 2025, 17 pages (with English Translation).
Office Action in Russian Patent Application No. 2022134723, dated Feb. 27, 2025, 28 pages (with English Translation).
Sergeev et al., "Short Course in Molecular Pharmacology," Moscow, 1975, p. 10, 3 pages (with English Translation).
Wesserling et al., "Will In Vitro Tests Replace Animal Models in Experimental Oncology?," Journal of Tissue Science and Engineering, 2011, 2(1):202e, pp. 1-4.
Submission Document in Japanese Patent Application No. P2022-559159, dated Dec. 22, 2025, 13 pages (with English translation).

(56) References Cited

OTHER PUBLICATIONS

Office Action in Chinese Patent Application No. 202210570963.X, dated Feb. 20, 2025, 10 pages (with English Translation).
Submission Document in Singaporean Patent Application No. 10201913213W, dated Mar. 12, 2025, 6 pages.
Cheng et al., "An overview of the binding models of FGFR tyrosine kinases in complex with small molecule inhibitors," European Journal of Medicinal Chemistry, 2017, 126:476-490.
Kawano et al., "Antitumor Activity of Tasurgratinib as an Orally Available FGFR1-3 Inhibitor in Cholangiocarcinoma Models With FGFR2-fusion," Anticancer Research, 2024, 44:2393-2406.
Submission Document in European Patent Application No. 21850938.8, dated Sep. 23, 2024, 12 pages (Response to the Communication pursuant to Rule 70(2)).
Submission Document in European Patent Application No. 21850938.8, dated Sep. 23, 2024, 39 pages (Response to the Invitation to file a translation of a previous application pursuant to R.53(3) EPC, Translations of the priority documents (JP2020130935 and JP2020163258)).
Notice of Allowance in U.S. Appl. No. 16/225,772, dated Mar. 27, 2025, 7 pages.
Notice of Allowance in U.S. Appl. No. 16/225,772, dated May 9, 2025, 7 pages.
Submission Document in Chinese Patent Application No. 202210570963.X, dated May 20, 2025, 8 pages (with English Translation).
Submission Document in U.S. Appl. No. 15/771,193, dated Apr. 30, 2025, 11 pages.
Notice of Allowance in Russian Patent Application No. 2024102267, dated Nov. 10, 2025, 18 pages (with English translation).
Office Action in Australian Patent Application No. 2021255084, dated Jan. 16, 2026, 4 pages.
Notice of Allowance in U.S. Appl. No. 15/547,139, dated Mar. 2, 2026, 11 pages.
Submission Document in Australian Patent Application No. 2021255084, dated Mar. 4, 2026, 2 pages.
European Search Report in European Patent Application No. 22864455.5, dated Apr. 30, 2025, 16 pages.
European Search Report in European Patent Application No. 22864456.3, dated Apr. 30, 2025, 11 pages.
Office Action in Taiwanese Patent Application No. 110139617, dated Jul. 24, 2025, 6 pages (with English translation).
Kwapisz, "Cyclin-dependent kinase 4/6 inhibitors in breast cancer: palbociclib, ribociclib, and abemaciclib," Breast Cancer Research and Treatment, Nov. 2017,166:41-54.
Nomura et al., "Endocrine Adjuvant Therapy with the Antiestrogen, Mepitiostane, in Operable Breast Cancer Patients on the Basis of Estrogen Receptor Assay," GANN, Apr. 30, 1978, 69(2):281-282.
Notice of Allowance in U.S. Appl. No. 15/771,193, dated May 14, 2025, 12 pages.
Office Action in Chinese Patent Application No. 202180072012.3, dated Apr. 25, 2025, 20 pages (with English Translation).
Office Action in U.S. Appl. No. 17/918,829, dated May 22, 2025, 76 pages.
Office Action in U.S. Appl. No. 18/008,304, dated May 15, 2025, 98 pages.
Notice of Allowance in United States U.S. Appl. No. 15/547,139, dated May 28, 2024, 14 pages.
Submission Document in European Patent Application No. 21787967.5, dated May 13, 2024, 15 pages.
Submission Document in United States U.S. Appl. No. 15/771,193, dated Mar. 25, 2024, 9 pages.
Submission Document in Chinese Patent Application No. 202210570963.X, dated Nov. 3, 2025, 9 pages (with English translation).
Office Action in Mexican Patent Application No. MX/a/2022/012934, dated Jun. 12, 2025, 14 pages (with English translation).
Office Action in Canadian Patent Application No. 3185174, dated Feb. 17, 2026, 9 pages.
Office Action in Chinese Patent Application No. 202180072012.3, dated Jan. 16, 2026, 20 pages (with English translation).
Bardia et al., "EMERALD: Phase III trial of elacestrant (RAD1901) vs endocrine therapy for previously treated ER+ advanced breast cancer," Future Oncol., Aug. 20, 2019, 15(28):3209-3218.
Brown et al., "CDK2 inhibition with BLU-222 in combination with ribociclib demonstrates robust antitumor activity in pre-clinical models of CDK4/6 inhibitor-naïve and -resistant HR+/HER2− breast cancer," Abstract P6-10-07, Presented at the Proceedings of the 2022 San Antonio Breast Cancer Symposium, San Antonio, TX, Dec. 6-10, 2022; Cancer Research, Mar. 2023, 83(5 Suppl), 1 page.
De Boisferon et al., "Tumor-specific molecular changes in luminal B breast cancer patient-derived xenografts (PDXs) with acquired resistance to endocrine treatment," Abstract #1399, Presented at the Proceedings of the American Association for Cancer Research Annual Meeting 2021 (AACR), Philadelphia, PA, Apr. 10-15 and May 17-21, 2021; Cancer Research, Jul. 2021, 81(13), 1 page.
Office Action in Canadian Patent Application No. 3180128, dated Dec. 12, 2025, 6 pages.
Office Action in U.S. Appl. No. 18/008,304, dated Dec. 10, 2025, 29 pages.
Notice of Allowance in U.S. Appl. No. 16/225,772, dated Jun. 17, 2025, 7 pages.
Notice of Allowance in Japanese Patent Application No. P2022-539547, dated Dec. 9, 2025, 7 pages (with English translation).
Submission Document in U.S. Appl. No. 16/225,772, dated Dec. 18, 2024, 2 pages.
Office Action in Chinese Patent Application No. 202180045666.7, dated Jul. 30, 2025, 17 pages (with English translation).
Office Action in Japanese Patent Application No. 2022-515429, dated Jul. 29, 2025, 8 pages (with English translation).
Submission Document in Russian Patent Application No. 2022127618, dated Jul. 9, 2025, 13 pages (with English translation).
Notice of Allowance in U.S. Appl. No. 16/225,772, dated Jun. 26, 2024, 14 pages.
Notice of Allowance in Australian Patent Application No. 2021255084, dated Mar. 19, 2026, 3 pages.
Submission Document in Korean Patent Application No. 10-2022-7039422, dated Mar. 4, 2026, 32 pages (with English translation).
Kawano et al., "Effect of Tasurgratinib as an Orally Available FGFR1-3 Inhibitor on Resistance to a CDK4/6 Inhibitor and Endocrine Therapy in ER+/HER2− Breast Cancer Preclinical Models," Cancers, Mar. 24, 2025, 17(7):1084, 16 pages.
Office Action in Taiwanese Patent Application No. 110127880, dated Oct. 9, 2025, 10 pages (with English translation).
Submission Document in Chinese Patent Application No. 202180045666.7, dated Oct. 24, 2025, 12 pages (with English translation).
Submission Document in Japanese Patent Application No. P2022-539547, dated Oct. 14, 2025, 64 pages (with English translation).
Notice of Allowance in U.S. Appl. No. 15/547,139, dated Jul. 11, 2025, 12 pages.
Submission Document in Taiwanese Patent Application No. 110139617, dated Jan. 21, 2026, 14 pages (with English translation).
Notice of Allowance in U.S. Appl. No. 15/771,193, dated Sep. 12, 2024, 5 pages.
Notice of Allowance in U.S. Appl. No. 16/225,772, dated Sep. 20, 2024, 21 pages.
Notice of Allowance in U.S. Appl. No. 15/547,139, dated Oct. 30, 2025, 11 pages.
Office Action in Japanese Patent Application No. P2022-515429, dated Oct. 21, 2025, 7 pages (with English translation).
European Search Report in European Application No. 21886203.5, dated Sep. 4, 2024, 10 pages.
Submission Document in Taiwanese Patent Application No. 110127880, dated Jul. 4, 2025, 17 pages (with English Translation).
"Cancer classification, NCI, from internet," 2008, p. 1-p. 3.
[No Author Listed], "Process Chemistry It is," from Pharmaceutical Synthesis to Manufacturing, 2nd Edition, 2014, pp. 143-144, Maruzen Publication Inc., Co., 5 pages (with partial English Translation).
[No Author], "Guidance for Industry—Estimating the Maximum Safe Starting Dose in Initial Clinical Trials for Therapeutics in Adult Healthy Volunteers," U.S. Department of Health and Human Ser-

(56) References Cited

OTHER PUBLICATIONS vices, Food and Drug Administration, Center for Drug Evaluation and Research (CDER), Pharmacology and Toxicology, Jul. 2005, 30 pages.
[No Author], "Progress on molecular mechanism of liver cancer in general surgery department of Ruijin Hospital, Shanghai Jiaotong University School Of Medicine," Journal of Shanghai Jiaotong University (Medical Science), 2016, 36(7):1022 (with English Translation).
Andre et al., "Targeting FGFR with Dovitinib (TKI258): Preclinical and Clinical Data in Breast Cancer", Clinical Cancer Research, vol. 19, No. 13, 2013.07.01, p. 3693-p. 3702.
Applicant's unpublished experimental data, 2014, 1 page.
Arai et. al, "Fibroblast Growth Factor Receptor 2 Tyrosine Kinase Fusions Define a Unique Molecular Subtype of Cholangiocarcinoma", Hepatology, 2014, vol. 59, No. 4, p. 1427-p. 1434.
Berrada et al., "Treatment of triple-negative metastatic breast cancer: toward individualized targeted treatments or chemosensitization? ," Annals of Oncology, vol. 21, Supplement 7, 2010, pvii30-pvii35.
Bono et al., "Inhibition of Tumor Angiogenesis and Growth by a Small-Molecule Multi-FGF Receptor Blocker with Allosteric Properties", Cancer Cell, 2013, p. 477-p. 488.
Borad et al., "Integrated Genomic Characterization Reveals Novel, Therapeutically Relevant Drug Targets in FGFR and EGFR Pathways in Sporadic Intrahepatic Cholangiocarcinoma", Plos Genetics, 2014, vol. 10, Issue 2, p. 1-p. 21.
Bøttcher et al., "Treatment of advanced HR+/HER2-breast cancer with new targeted agents in combination with endocrine therapy: a review of efficacy and tolerability based on available randomized trials on everolimus, ribociclib, palbociclib and abemaciclib," Acta Oncologica, 2019, 58(2):147-153.
Bucci et al., "Circadian Rhythms: channels contribute," Nature Chem Bio., Jun. 2013, 9:349.
Cancer Genome Atlas Research Network, "Comprehensive genomic characterization of squamous cell lung cancers," Nature, 2012, 489(7417):519-525.
Celina Ang, "Role of the fibroblast growth factor receptor axis incholangiocarcinoma", Journal of Gastroenterology and Hepatology, 2015, vol. 30, p. 1116-p. 1122.
Chen et al., "Anti-PD-1/PD-L1 therapy of human cancer: past, present, and future," The Journal of Clinical Investigation, 2015, 125(9):3384-3391.
Chen et al., "Inhibition of endogenous SPARC enhances pancreatic-cancer cell growth: modulation by FGFR1-III isoform expression", Br J Cancer, 2010(102), p. 188-p. 195.
Choi et al., "Molecular Targeted Therapy for Hepatocellular Carcinoma: Present Status and Future Directions," Biological and Pharmaceutical Bulletin, 2015, 38:986-991.
ClinicalTrials.gov [online], "History of Changes for Study: NCT02275910 Phase 1 Study of E7090 in Subjects With Solid Tumor," Versions A & B of Jun. 26, 2017, retrieved from: URL<https://clinicaltrials.gov/ct2/history/NCT02275910?A=5&B-5&C-merged#StudyPageTop>, 4 pages.
Daniele et al., "FGF Receptor Inhibitors: Role in Cancer Therapy", Curr Oncol Rep., 2012(14), p. 111-p. 119.
Deeks et al., "Exemestane—A Review of its Use in Postmenopausal Women with Breast Cancer," Drugs, 2009, 69(7):889-918.
Dey et al., "Targeting Fibroblast Growth Factor Receptors Blocks PI3K/AKT Signaling, Induces Apoptosis, and Impairs Mammary Tumor Outgrowth andlMetastasis," Cancer Research, vol. 70, No. 10, May 15, 2010, p. 4151-p. 4162.
European Search Report in European Application No. 14754294.8, dated Jul. 15, 2016, 5 pages.
European Search Report in European Application No. 15834302.0, dated Mar. 15, 2018, 6 pages.
European Search Report in European Application No. 16768810.0, dated Aug. 17, 2018, 7 pages.
European Search Report in European Application No. 16768810.0, dated Dec. 11, 2018, 7 pages.
European Search Report in European Application No. 16875716.9, dated Jul. 29, 2019, 9 pages.
European Search Report in European Application No. 18865416.4, dated May 28, 2021, 9 pages.
European Search Report in European Application No. 19777797.2, dated Nov. 15, 2021, 8 pages.
European Search Report in European Application No. 21787967.5, dated Feb. 16, 2024, 9 pages.
European Search Report in European Application No. 21850938.8, Mar. 6, 2024, 8 pages.
Formisano et al., "Aberrant FGFR signaling mediates resistance to CDK4/6 inhibitors in ER+ breast cancer," Nature Communications, 2019, 10:1373, 14 pages.
Formisano et al., "Association of FGFR1 with ERa Maintains Ligand-Independent ER Transcription and Mediates Resistance to Estrogen Deprivation in ER+ Breast Cancer," Clinical Cancer Research, 2017, 23(20):6138-6150.
Forner et al., "Hepatocellular Carcinoma," The Lancet, Mar. 2012, 379:1245-1255.
Foulkes et al., "Triple-Negative Breast Cancer," The New England Journal of Medicine, Nov. 11, 2010, 363:1938-1948.
French et al., "Targeting FGFR4 Inhibits Hepatocellular Carcinoma in Preclinical Mouse Models", PLoS One, 2012(7), p. 1-p. 12.
Futami et al., "ASP5878, a Novel Inhibitor of FGFR1, 2, 3, and 4, Inhibits the Growth of FGF19-Expressing Hepatocellular Carcinoma," Molecular Cancer Therapeutics, 2017, 16(1):68-75, XP055858063.
Gavine et al., "AZD4547: An Orally Bioavailable, Potent, and Selective Inhitor of the Fibroblast Growth Factor Receptor Tyrosine Kinase Family", Cancer Res, 2012(72), p. 2045-p. 2056.
Gould, "Salt selection for basic drugs," International Journal of Pharmaceutics, 1986, 33:201-217.
Guagnano et al., "Discovery of 3-(2,6-Dichloro-3,5-dimethoxyphenyl)-1-{6-[4-(4-ethyl-piperazin-1-yl)-phenylamino]-pyrimidin-4-y1}-1-methyl-urea (NVP-BGJ398), A Potent and Selective Inhibitor of the Fibroblast Growth Factor Receptor Family of Receptor Tyrosine Kinase", J Med Chem, 2011(54).
Guagnano et al., "FGFR Genetic Alterations Predict for Sensitivity to NVP-BGJ398, a Selective Pan-FGFR Inhibitor", Cancer Discovery, Sep. 20, 2012, p. 1118-p. 1133.
Harbinski et al., "Rescue Screens with Secreted Proteins Reveal Compensatory Potential of Receptor Tyrosine Kinases in Driving Cancer Growth", Cancer Discovery, Aug. 8, 2012, p. 948-p. 958.
Howell et al., "Comparison of fulvestrant versus tamoxifen for the treatment of advanced breast cancer in postmenopausal women previously untreated with endocrine therapy: a multinational, double-blind, randomized trial," Journal of Clinical Oncology, 2004, 22(9):1605-1613.
Imamura et al., "Regioselective cleavage Reaction of the Aromatic methylenedioxy Ring. V. Cleavage with Sodium Alkoxides-Alcohols, Potassium tert-Butoxide-Alcohols, Dimsyl Anion-Methyl Alcohol, Metallic Sodium-Alcohols, and Sodium Cyanide in Dipolar Aprotic Solvents," Chemical & Pharmaceutical Bulletin, 1992, 40(7):1691-1696.
International Preliminary Report on Patentability in International Application No. PCT/JP2014/053819, dated Sep. 3, 2015, 7 pages.
International Preliminary Report on Patentability in International Application No. PCT/JP2015/073047, dated Mar. 2, 2017, 6 pages (English Translation).
International Preliminary Report on Patentability in International Application No. PCT/JP2019/012971, dated Oct. 8, 2020, 8 pages.
International Preliminary Report on Patentability in International Application No. PCT/JP2022/032309, dated Mar. 14, 2024, 7 pages.
International Preliminary Report on Patentability in International Application No. PCT/JP2022/032310, dated Mar. 14, 2024, 7 pages.
International Preliminary Report on Patentability in Patent Application No. PCT/JP2016/059162, dated Oct. 5, 2017, 8 pages (English Translation).
International Preliminary Report on Patentability in Patent Application No. PCT/JP2016/087349, dated Jun. 28, 2018, 9 pages.
International Preliminary Report on Patentability in Patent Application No. PCT/JP2021/028008, dated Feb. 9, 2023, 6 pages.

(56) References Cited

OTHER PUBLICATIONS

International Preliminary Report on Patentability in Patent Application No. PCT/JP2021/039490, dated May 11, 2023, 6 pages.
International Search Report and Written Opinion in International Application No. PCT/JP2019/012971, dated May 14, 2019, 11 pages (with Partial Translation).
International Search Report and Written Opinion in International Application No. PCT/JP2021/028008, dated Aug. 31, 2021 21 pages (with English Translation).
International Search Report in International Application No. PCT/JP2014/053819, dated Apr. 15, 2014, 9 pages.
International Search Report in International Application No. PCT/JP2015/073047 dated Nov. 17, 2015, 2 pages (English translation).
International Search Report in International Application No. PCT/JP2016/059162, dated May 24, 2016, 2 pages (English Translation).
International Search Report in International Application No. PCT/JP2016/087349, dated Feb. 7, 2017, 2 pages (English Translation).
International Search Report in International Application No. PCT/JP2018/037690, dated Jan. 15, 2019, 7 pages.
International Search Report in International Application No. PCT/JP2019/012971, dated May 14, 2019, 9 pages.
International Search Report in International Application No. PCT/JP2021/015546, dated May 25, 2021, 4 pages (with English Translation).
International Search Report in International Application No. PCT/JP2021/028008, dated Aug. 31, 2021, 6 pages (with English Translation).
International Search Report in International Application No. PCT/JP2021/039490, dated Dec. 14, 2021, 4 pages (with English Translation).
International Search Report in International Application No. PCT/JP2022/032309, dated Nov. 15, 2022, 5 pages.
International Search Report in International Patent Application No. PCT/JP2022/032310, dated Nov. 15, 2022, 5 pages.
Ishiwata et al., "Enhanced Expression of Fibroblast Growth Factor Receptor 2 IIIc Promotes Human Pancreatic Cancer Cell Proliferation", Am J Pathol, 2012(180), p. 1928-p. 1941.
Katoh, "Fibroblast growth factor receptors as treatment targets in clinical oncology," Nature Reviews, Clinical Oncology, 2019, 16(2):105-122.
Kim et al., "Regorafenib in advanced hepatocellular carcinoma (HCC): considerations for treatment," Cancer Chemotherapy and Pharmacology, 2017, 80:945-954.
Koyama et al., "Abstract B160: First-in-human phase 1 study of E7090, a novel selective inhibitor of FGFRs, in patients with advanced solid tumors," Abstract, AACR-NCI-EORTC International Conference: Molecular Targets and Cancer Therapeutics, Jan. 2018, [Retrieved on May 18, 2021], retrieved from: URL<https://mct.aacrjournals.org/content/17/1_Supplement/B160>, 4 pages.
Koziczak et al., "Blocking of FGFR signaling inhibits breast cancer cell proliferation through downregulation of D-type cyclins", Oncogene, vol. 23, 2004, p. 3501-p. 3508.
Li et al., "Preparation of heteroaryls for therapeutic use in pharmaceutical compositions as kinase inhibitors for treatment of hyperproliferative diseases, including cancer," 2003, CA139:323437.
Li et al., "Research and Development Progress on the Relationship between Small Molecule Anti-Tumor FGFR Inhibitor and FGFR Protein," Acta Pharmaceutica Sinica, 2016, 51(11):1689-1697 (with English Translation).
Llovet et al., "Sorafenib in Advanced Hepatocellular Carcinoma," The New England Journal of Medicine, 2008, 359:378-390.
Logie et al., "Activating mutations of the tyrosine kinase receptor FGFR3 are associated with benign skin tumors in mice and humans", Hum Mol Genet, 2005(14), p. 1153-p. 1160.
Miyano et al., "E7090, a novel selective inhibitor of fibroblast growth factor receptors, displays potent antitumor activity and prolongs survival in preclinical models," Molecular Cancer Therapeutics, 2016, 15(11):2630-2639.
Mohammadi et al., "Crystal structure of an angiogenesis inhibitor bound to the FGF receptor tyrosine kinase domain", The EMBO Journal vol. 17 No. 20, 1998, p. 5896-p. 5904.
Mouron et al., "FGFR1 amplification or overexpression and hormonal resistance in luminal breast cancer: rationale for a triple blockade of ER, CDK4/6, and FGFRI," Breast Cancer Research (Online Edition), Feb. 12, 2021, 23(1):1-16.
Musolino et al., "Phase II, randomized, placebo-controlled study of dovitinib in combination with fulvestrant in postmenopausal patients with $HR^+$, $HER2^-$ breast cancer that had progressed during or after prior endocrine therapy," Breast Cancer Research, 2017, 19:18.
Nayar et al., "Acquired HER2 mutations in $ER^+$ metastatic breast cancer confer resistance to estrogen receptor-directed therapies," Nature Genetics, 2019, 51:207-216.
Nicholas et al., "Fibroblast growth factor signalling:from development to cancer", Nature Reviews Cancer, 2010(10), p. 116-p. 129.
Norman et al., "Protein-Ligand Crystal Structures Can Guide the Design of Selective Inhibitors of the FGFR Tyrosine Kinase", Journal of Medicinal Chemistry, May 21, 2012, p. 5003-p. 5012.
Notice of Allowance in Australian Patent Application No. 2014219811, dated Sep. 13, 2017, 3 pages.
Notice of Allowance in Australian Patent Application No. 2015304465, dated Apr. 24, 2019, 3 pages.
Notice of Allowance in Australian Patent Application No. 2016237222, dated Apr. 16, 2021, 4 pages.
Notice of Allowance in Australian Patent Application No. 2016374441, dated Oct. 8, 2021, 3 pages.
Notice of Allowance in Brazilian Patent Application No. BR112015019790-6, dated Aug. 11, 2020, 2 pages (with English Translation).
Notice of Allowance in Brazilian Patent Application No. BR1120170163926, dated Jan. 3, 2023, 6 pages (with English Translation).
Notice of Allowance in Brazilian Patent Application No. BR1120180101036, dated Apr. 11, 2023, 7 pages (with English translation).
Notice of Allowance in Canadian Patent Application No. 2901585, dated Jun. 5, 2019, 1 page (with English Translation).
Notice of Allowance in Canadian Patent Application No. 2956270, dated Apr. 12, 2022, 1 page (with English Translation).
Notice of Allowance in Canadian Patent Application No. 2974937, dated Jun. 2, 2023, 1 page (with English Translation).
Notice of Allowance in Canadian Patent Application No. 3001969, dated May 26, 2023, 1 page (with English Translation).
Notice of Allowance in Chilean Patent Application No. 2015-02311, dated Dec. 12, 2019, 6 pages (with English Translation).
Notice of Allowance in Chinese Patent Application No. 201480009370.X dated Jul. 25, 2017, 4 pages (English Translation).
Notice of Allowance in Chinese Patent Application No. 201580042132.3, dated Mar. 6, 2019, 4 pages (with English Translation).
Notice of Allowance in European Patent Application No. 14754294.8, dated Jan. 4, 2017, 239 pages.
Notice of Allowance in European Patent Application No. 14754294.8, dated Mar. 9, 2017, 2 pages.
Notice of Allowance in European Patent Application No. 15834302.0, dated Dec. 22, 2021, 56 pages.
Notice of Allowance in European Patent Application No. 15834302.0, dated Oct. 21, 2021, 56 pages.
Notice of Allowance in European Patent Application No. 16768810.0, dated Mar. 16, 2021, 71 pages.
Notice of Allowance in European Patent Application No. 16875716.9, dated Oct. 28, 2020, 18 pages.
Notice of Allowance in Gulf Cooperation Council Patent Application GCC/P/2014/26467, dated Jan. 7, 2018, 2 pages (English Translation).
Notice of Allowance in Indonesian Patent Application No. P-00201505035, dated Sep. 27, 2019, 4 pages (with English Translation).
Notice of Allowance in Israeli Patent Application No. 240623, dated Jan. 7, 2019, 7 pages (English Translation).
Notice of Allowance in Israeli Patent Application No. 250290, dated Mar. 17, 2020, 10 pages (with English Translation).

(56) References Cited

OTHER PUBLICATIONS

Notice of Allowance in Israeli Patent Application No. 253701, dated Nov. 11, 2020, 9 pages (with English Translation).
Notice of Allowance in Japanese Patent Application No. P2015-560425, dated Apr. 19, 2016, 6 pages (English Translation).
Notice of Allowance in Japanese Patent Application No. P2017-508383, dated Mar. 5, 2019, 6 pages (with English Translation).
Notice of Allowance in Japanese Patent Application No. P2017-556119, dated Mar. 16, 2021, 6 pages (with English Translation).
Notice of Allowance in Japanese Patent Application No. P2023-504017, dated Jul. 11, 2023, 5 pages (with English Translation).
Notice of Allowance in Japanese Patent Application No. P2023-504019, dated Jul. 11, 2023, 5 pages (with English Translation).
Notice of Allowance in Jordanian Patent Application No. 39/2014, dated Apr. 16, 2018, 2 pages (with English Translation).
Notice of Allowance in Korean Patent Application No. 10-2015-7022252, dated Nov. 11, 2019, 5 pages (with English Translation).
Notice of Allowance in Korean Patent Application No. 10-2017-7002791, dated Nov. 29, 2021, 3 pages (with English Translation).
Notice of Allowance in Korean Patent Application No. 10-2017-7021185, dated Apr. 27, 2023, 7 pages (with English Translation).
Notice of Allowance in Korean Patent Application No. 10-2018-7014626, dated Dec. 19, 2022, 6 pages (with English Translation).
Notice of Allowance in Malaysian Patent Application No. PI2015702696, dated Jul. 9, 2020, 2 pages (with English Translation).
Notice of Allowance in Mexican Patent Application No. MX/a/2015/010698, dated Nov. 8, 2018, 4 pages (English Translation).
Notice of Allowance in Mexican Patent Application No. MX/a/2017/001624, dated Oct. 23, 2019, 5 pages (with English Translation).
Notice of Allowance in Mexican Patent Application No. MX/a/2017/009892, dated Dec. 15, 2020, 6 pages (with English Translation).
Notice of Allowance in Mexican Patent Application No. MX/a/2020/008610, dated Jul. 15, 2022, 4 pages (with English Translation).
Notice of Allowance in New Zealand Patent Application No. 711101, dated Jul. 27, 2018, 1 page.
Notice of Allowance in Pakistani Patent Application No. 523/2016, dated Dec. 31, 2019, 3 pages.
Notice of Allowance in Pakistani Patent Application No. 94/2014, dated Dec. 31, 2019, 3 pages.
Notice of Allowance in Russian Patent Application No. 2015134558, dated Jan. 10, 2018, 25 pages (English Translation).
Notice of Allowance in Russian Patent Application No. 2017103439, dated Apr. 10, 2018, 14 pages (English Translation).
Notice of Allowance in Russian Patent Application No. 2017127135, dated Dec. 17, 2019, 16 pages (with English Translation).
Notice of Allowance in Russian Patent Application No. 2018119102, dated Jun. 26, 2020, 12 pages (with English Translation.
Notice of Allowance in Russian Patent Application No. 2020127993, dated May 4, 2022, 12 pages (with English Translation).
Notice of Allowance in Singaporean Patent Application No. 11201506488W, dated Sep. 20, 2017 (English Translation).
Notice of Allowance in Singaporean Patent Application No. 11201700703X, dated Sep. 12, 2017, 5 pages (English Translation).
Notice of Allowance in Singaporean Patent Application No. 11201706143S, dated Oct. 29, 2020, 4 pages.
Notice of Allowance in South African Application No. 2015/05941, dated May 24, 2016, 6 pages.
Notice of Allowance in Taiwanese Application No. 103105419, dated Sep. 11, 2018, 5 pages (English Translation).
Notice of Allowance in Taiwanese Application No. 107134522, dated Jul. 29, 2019, 7 pages (with English Translation).
Notice of Allowance in Taiwanese Application No. 107134526, dated Jul. 29, 2019, 7 pages (with English Translation).
Notice of Allowance in Taiwanese Application No. 107134529, dated Jul. 29, 2019, 7 pages (with English Translation).
Notice of Allowance in Ukrainian Patent Application a201508149, dated Jan. 3, 2018, 16 pages (English Translation).
Notice of Allowance in U.S. Appl. No. 14/183,864, dated Nov. 19, 2014, 11 pages.
Notice of Allowance in U.S. Appl. No. 15/500,429, dated Jan. 18, 2018, 6 pages.
Notice of Allowance in U.S. Appl. No. 15/500,429, dated Mar. 29, 2018, 4 pages.
Notice of Allowance in U.S. Appl. No. 15/500,429, dated Oct. 19, 2017, 11 pages.
Notice of Allowance in U.S. Appl. No. 15/547,139, dated Apr. 10, 2023, 23 pages.
Notice of Allowance in U.S. Appl. No. 15/547,139, dated Aug. 23, 2023, 15 pages.
Notice of Allowance in U.S. Appl. No. 15/547,139, dated Aug. 7, 2019, 17 pages.
Notice of Allowance in U.S. Appl. No. 15/547,139, dated Dec. 22, 2023, 6 pages.
Notice of Allowance in U.S. Appl. No. 15/547,139, dated Dec. 31, 2019, 13 pages.
Notice of Allowance in U.S. Appl. No. 15/547,139, dated Dec. 5, 2019, 20 pages.
Notice of Allowance in U.S. Appl. No. 15/547,139, dated Feb. 28, 2024, 6 pages.
Notice of Allowance in U.S. Appl. No. 15/547,139, dated Feb. 5, 2021, 23 pages.
Notice of Allowance in U.S. Appl. No. 15/547,139, dated Feb. 6, 2024, 6 pages.
Notice of Allowance in U.S. Appl. No. 15/547,139, dated Jan. 19, 2024, 7 pages.
Notice of Allowance in U.S. Appl. No. 15/547,139, dated Jul. 25, 2022, 22 pages.
Notice of Allowance in U.S. Appl. No. 15/547,139, dated Jun. 23, 2020, 11 pages.
Notice of Allowance in U.S. Appl. No. 15/547,139, dated Mar. 24, 2020, 23 pages.
Notice of Allowance in U.S. Appl. No. 15/547,139, dated Mar. 4, 2022, 25 pages.
Notice of Allowance in U.S. Appl. No. 15/547,139, dated Mar. 6, 2019, 13 pages.
Notice of Allowance in U.S. Appl. No. 15/547,139, dated May 12, 2021, 12 pages.
Notice of Allowance in U.S. Appl. No. 15/547,139, dated Nov. 17, 2022, 14 pages.
Notice of Allowance in U.S. Appl. No. 15/547,139, dated Oct. 20, 2021, 12 pages.
Notice of Allowance in U.S. Appl. No. 15/547,139, dated Oct. 23, 2023, 7 pages.
Notice of Allowance in U.S. Appl. No. 15/547,139, dated Oct. 4, 2021, 24 pages.
Notice of Allowance in U.S. Appl. No. 15/547,139, dated Oct. 4, 2023, 7 pages.
Notice of Allowance in U.S. Appl. No. 15/547,139, dated Sep. 28, 2018, 16 pages.
Notice of Allowance in U.S. Appl. No. 15/771,193, dated Apr. 4, 2024, 17 pages.
Notice of Allowance in U.S. Appl. No. 15/771,193, dated Aug. 27, 2021, 26 pages.
Notice of Allowance in U.S. Appl. No. 15/771,193, dated Dec. 10, 2021, 42 pages.
Notice of Allowance in U.S. Appl. No. 15/771,193, dated Dec. 26, 2023, 13 pages.
Notice of Allowance in U.S. Appl. No. 15/771,193, dated Feb. 17, 2023, 15 pages.
Notice of Allowance in U.S. Appl. No. 15/771,193, dated Feb. 4, 2021, Feb. 4, 2021, 15 pages.
Notice of Allowance in U.S. Appl. No. 15/771,193, dated Jul. 10, 2023, 6 pages.
Notice of Allowance in U.S. Appl. No. 15/771,193, dated Jul. 12, 2022, 4 pages.
Notice of Allowance in U.S. Appl. No. 15/771,193, dated Jul. 6, 2022, 19 pages.

(56) References Cited

OTHER PUBLICATIONS

Notice of Allowance in U.S. Appl. No. 15/771,193, dated Jun. 14, 2023, 14 pages.
Notice of Allowance in U.S. Appl. No. 15/771,193, dated Mar. 24, 2022, 14 pages.
Notice of Allowance in U.S. Appl. No. 15/771,193, dated May 11, 2021, 12 pages.
Notice of Allowance in U.S. Appl. No. 15/771,193, dated Oct. 22, 2020, 29 pages.
Notice of Allowance in U.S. Appl. No. 15/771,193, dated Oct. 26, 2022, 14 pages.
Notice of Allowance in U.S. Appl. No. 15/771,193, dated Sep. 20, 2023, 11 pages.
Notice of Allowance in U.S. Appl. No. 16/225,772, dated Apr. 14, 2020, 22 pages.
Notice of Allowance in U.S. Appl. No. 16/225,772, dated Apr. 2, 2024, 15 pages.
Notice of Allowance in U.S. Appl. No. 16/225,772, dated Apr. 20, 2022, 13 pages.
Notice of Allowance in U.S. Appl. No. 16/225,772, dated Apr. 7, 2022, 11 pages.
Notice of Allowance in U.S. Appl. No. 16/225,772, dated Dec. 16, 2019, 9 pages.
Notice of Allowance in U.S. Appl. No. 16/225,772, dated Dec. 21, 2021, 38 pages.
Notice of Allowance in U.S. Appl. No. 16/225,772, dated Dec. 6, 2023, 39 pages.
Notice of Allowance in U.S. Appl. No. 16/225,772, dated Jan. 11, 2022, 9 pages.
Notice of Allowance in U.S. Appl. No. 16/225,772, dated Jan. 12, 2023, 27 pages.
Notice of Allowance in U.S. Appl. No. 16/225,772, dated Jan. 15, 2020, 9 pages.
Notice of Allowance in U.S. Appl. No. 16/225,772, dated Jan. 24, 2023, 7 pages.
Notice of Allowance in U.S. Appl. No. 16/225,772, dated Jul. 12, 2021, 14 pages.
Notice of Allowance in U.S. Appl. No. 16/225,772, dated Jul. 23, 2021, 10 pages.
Notice of Allowance in U.S. Appl. No. 16/225,772, dated Jul. 24, 2020, 10 pages.
Notice of Allowance in U.S. Appl. No. 16/225,772, dated Jun. 14, 2023, 8 pages.
Notice of Allowance in U.S. Appl. No. 16/225,772, dated Mar. 29, 2021, 22 pages.
Notice of Allowance in U.S. Appl. No. 16/225,772, dated May 17, 2023, 13 pages.
Notice of Allowance in U.S. Appl. No. 16/225,772, dated May 26, 2023, 9 pages.
Notice of Allowance in U.S. Appl. No. 16/225,772, dated Oct. 22, 2019, 19 pages.
Notice of Allowance in U.S. Appl. No. 16/225,772, dated Sep. 21, 2022, 10 pages.
Notice of Allowance in U.S. Appl. No. 16/225,772, dated Sep. 8, 2022, 23 pages.
Notice of Allowance in U.S. Appl. No. 16/970,683, dated Apr. 16, 2021, 11 pages.
Notice of Allowance in U.S. Appl. No. 16/970,683, dated Feb. 10, 2021, 5 pages.
Notice of Allowance in U.S. Appl. No. 16/970,683, dated Jan. 15, 2021, 9 pages.
Notice of Allowance in U.S. Appl. No. 16/970,683, dated Jul. 30, 2021, 12 pages.
Notice of Allowance in U.S. Appl. No. 16/970,683, dated Nov. 10, 2021, 6 pages.
Notice of Allowance in U.S. Appl. No. 16/970,683, dated Nov. 3, 2021, 16 pages.
Notice of Allowance in Vietnamese Patent Application No. 1-2015-02994, dated Oct. 23, 2017, 2 pages (English Translation).
Office Action in Argentine Patent Application No. P140100495, dated Jan. 22, 2021, 10 pages (with English Translation).
Office Action in Argentine Patent Application No. P140100495, dated Nov. 11, 2019, 4 pages (with English Translation).
Office Action in Argentine Patent Application No. P140100495, dated Sep. 6, 2022, 6 pages (with English Translation).
Office Action in Australian Patent Application No. 2014219811, dated Jun. 16, 2017, 2 pages.
Office Action in Australian Patent Application No. 2015304465, dated Jan. 21, 2019, 2 pages.
Office Action in Australian Patent Application No. 2016237222, dated Jan. 29, 2021, 4 pages.
Office Action in Australian Patent Application No. 2016237222, dated Sep. 2, 2020, 6 pages.
Office Action in Australian Patent Application No. 2016374441, dated May 31, 2021, 4 pages.
Office Action in Australian Patent Application No. 2018349961, dated Aug. 15, 2023, 4 pages.
Office Action in Australian Patent Application No. 2018349961, dated Jul. 19, 2022, 1 page.
Office Action in Brazilian Patent Application No. BR112015019790-6, dated Apr. 7, 2020, 14 pages (with English Translation).
Office Action in Brazilian Patent Application No. BR1120170022680, dated Apr. 7, 2020, 9 pages (with English Translation).
Office Action in Brazilian Patent Application No. BR1120170163926, dated Dec. 8, 2020, 10 pages (with English Translation).
Office Action in Brazilian Patent Application No. BR1120170163926, dated Oct. 11, 2022, 5 pages (with English Translation).
Office Action in Brazilian Patent Application No. BR1120180101036, dated Feb. 9, 2021, 9 pages (with English Translation).
Office Action in Brazilian Patent Application No. BR1120200038490, dated Sep. 13, 2022, 11 pages (with English Translation).
Office Action in Canadian Patent Application No. 2901585, dated Jan. 30, 2019, 3 pages.
Office Action in Canadian Patent Application No. 2956270, dated Apr. 22, 2021, 4 pages.
Office Action in Canadian Patent Application No. 2956270, dated Sep. 28, 2021, 3 pages.
Office Action in Canadian Patent Application No. 2974937, dated Dec. 6, 2022, 3 pages.
Office Action in Canadian Patent Application No. 2974937, dated May 2, 2022, 5 pages.
Office Action in Canadian Patent Application No. 3001969, dated Nov. 9, 2022, 4 pages.
Office Action in Chilean Patent Application No. 2015-02311, dated Mar. 22, 2017, 21 pages (English Translation).
Office Action in Chilean Patent Application No. 2015-02311, dated Sep. 13, 2017, 13 pages (English Translation).
Office Action in Chinese Patent Application No. 201480009370.X, dated Jan. 9, 2017, 10 pages (English Translation).
Office Action in Chinese Patent Application No. 201480009370.X, dated May 26, 2016, 7 pages (English Translation).
Office Action in Chinese Patent Application No. 201580042132.3, dated Aug. 8, 2018, 11 pages (English Translation).
Office Action in Chinese Patent Application No. 201680007472.7, dated Aug. 9, 2021, 10 pages (with English Translation).
Office Action in Chinese Patent Application No. 201680007472.7, dated Feb. 25, 2022, 14 pages (with English Translation).
Office Action in Chinese Patent Application No. 201680007472.7, dated Jan. 15, 2020, 8 pages (with English Translation).
Office Action in Chinese Patent Application No. 201680007472.7, dated Jun. 14, 2019, 14 pages (with English Translation).
Office Action in Chinese Patent Application No. 201680007472.7, dated May 6, 2020, 8 pages (with English Translation).
Office Action in Chinese Patent Application No. 201680068110.9, dated Jan. 24, 2022, 10 pages (with English Translation).
Office Action in Chinese Patent Application No. 201680068110.9, dated Jun. 1, 2022, 15 pages (with English Translation).
Office Action in Chinese Patent Application No. 201680068110.9, dated Mar. 20, 2020, 15 pages (with English Translation).
Office Action in Chinese Patent Application No. 201680068110.9, dated Nov. 24, 2020, 9 pages (with English Translation).

(56) References Cited

OTHER PUBLICATIONS

Office Action in Chinese Patent Application No. 201880055615.0, dated Aug. 1, 2022, 21 pages (with English Translation).
Office Action in Chinese Patent Application No. 201980013339.6, dated Feb. 12, 2023, 9 pages (with English Translation).
Office Action in Chinese Patent Application No. 201980013339.6, dated Oct. 10, 2022, 16 pages (with English Translation).
Office Action in Chinese Patent Application No. 202180028460.3 dated Jun. 12, 2023, 13 pages (English Translation).
Office Action in Chinese Patent Application No. 202180028460.3, dated Jan. 10, 2024, 9 pages (with English Translation).
Office Action in Chinese Patent Application No. 202180028460.3, dated Oct. 13, 2023, 10 pages (with English Translation).
Office Action in Egyptian Patent Application No. PCT1285/2015, dated Apr. 10, 2023, 8 pages (with English Translation).
Office Action in Egyptian Patent Application No. PCT1285/2015, dated Aug. 7, 2022, 10 pages (with English Translation).
Office Action in Egyptian Patent Application No. PCT1285/2015, dated Oct. 5, 2021, 11 pages (with English Translation).
Office Action in European Patent Application No. 15834302.0, dated May 14, 2021, 4 pages.
Office Action in European Patent Application No. 15834302.0, dated Oct. 28, 2019, 4 pages.
Office Action in European Patent Application No. 16768810.0, dated Jun. 18, 2020, 5 pages.
Office Action in Gulf Cooperation Council Patent Application No. GCC/P/2014/26467, dated Jun. 7, 2017, 7 pages (English Translation).
Office Action in Indian Patent Application No. 201747003469, dated Aug. 2, 2019, 5 pages (with English Translation).
Office Action in Indian Patent Application No. 201747003469, dated Jan. 8, 2021, 2 pages (with English Translation).
Office Action in Indian Patent Application No. 201747027065, dated Jan. 28, 2020, 6 pages (with English Translation).
Office Action in Indian Patent Application No. 201747027065, dated Jul. 8, 2020, 2 pages (with English Translation).
Office Action in Indian Patent Application No. 201847015401, dated Aug. 4, 2022, 3 pages (with English Translation).
Office Action in Indian Patent Application No. 201847015401, dated Dec. 22, 2023, 3 pages.
Office Action in Indian Patent Application No. 201847015401, dated Jun. 29, 2021, 3 pages (with English Translation).
Office Action in Indian Patent Application No. 201847015401, dated Mar. 8, 2024, 6 pages.
Office Action in Indian Patent Application No. 201847015401, dated May 5, 2020, 7 pages (with English Translation).
Office Action in Indian Patent Application No. 202047007881, dated Jun. 1, 2022, 3 pages (with English Translation).
Office Action in Indian Patent Application No. 202047007881, dated Nov. 12, 2021, 5 pages (with English Translation).
Office Action in Indian Patent Application No. 202047036696, dated Feb. 24, 2022, 6 pages (with English Translation).
Office Action in Indian Patent Application No. 202047036696, dated Jan. 11, 2023, 2 pages (with English Translation).
Office Action in Indian Patent Application No. 4989/CHENP/2015, dated Jan. 31, 2019, 5 pages (with English Translation).
Office Action in Indonesian Patent Application No. P-00201505035, dated Feb. 1, 2019, 5 pages, (with English Translation).
Office Action in Israeli Patent Application No. 240623, dated Dec. 20, 2017, 8 pages (English Translation).
Office Action in Israeli Patent Application No. 240623, dated Jan. 19, 2016, 5 pages (English Translation).
Office Action in Israeli Patent Application No. 250290, dated Aug. 15, 2019, 8 pages (with English Translation).
Office Action in Israeli Patent Application No. 250290, dated Jan. 29, 2020, 10 pages (with English Translation).
Office Action in Israeli Patent Application No. 250290, dated Sep. 2, 2018, 5 pages (English Translation).
Office Action in Israeli Patent Application No. 253701, dated Nov. 28, 2019, 7 pages (with English Translation).
Office Action in Israeli Patent Application No. 253701, dated Oct. 17, 2018, 7 pages (with English Translation).
Office Action in Israeli Patent Application No. 258671, dated Apr. 12, 2022, 12 pages (with English Translation).
Office Action in Israeli Patent Application No. 258671, dated Aug. 4, 2019, 5 page (with English Translation).
Office Action in Israeli Patent Application No. 258671, dated Jan. 19, 2023, 13 pages (with English Translation).
Office Action in Israeli Patent Application No. 258671, dated Jun. 25, 2020, 8 pages (with English Translation).
Office Action in Israeli Patent Application No. 258671, dated May 10, 2021, 18 pages (with English Translation).
Office Action in Israeli Patent Application No. 272887, dated Aug. 17, 2022, 3 pages.
Office Action in Israeli Patent Application No. 272887, dated Nov. 23, 2020, 5 pages (with English Translation).
Office Action in Israeli Patent Application No. 276935, dated Apr. 22, 2021, 5 pages (with English Translation).
Office Action in Israeli Patent Application No. 276935, dated Jan. 3, 2023, 4 pages (with English Translation).
Office Action in Japanese Application No. P2015-560425, dated Mar. 8, 2016, 4 pages (English Translation).
Office Action in Japanese Application No. P2017-556119, dated Sep. 8, 2020, 6 pages (with English Translation).
Office Action in Japanese Application No. P2020-510951, dated Jan. 4, 2023, 7 pages (with English Translation).
Office Action in Japanese Application No. P2020-512051, dated Mar. 7, 2023, 2 pages (with English Translation).
Office Action in Japanese Application No. P2020-512051, dated Sep. 13, 2022, 8 pages (with English Translation).
Office Action in Japanese Patent Application No. P2023-504017, dated Apr. 11, 2023, 6 pages (with English Translation).
Office Action in Japanese Patent Application No. P2023-504019, dated Apr. 11, 2023, 10 pages (with English Translation).
Office Action in Korean Patent Application No. 10-2015-7022252, dated Sep. 5, 2019, 11 pages (with English Translation).
Office Action in Korean Patent Application No. 10-2017-7002791, dated Aug. 29, 2021, 7 pages (with English Translation).
Office Action in Korean Patent Application No. 10-2017-7021185, dated Feb. 10, 2023, 10 pages (with English Translation).
Office Action in Mexican Patent Application No. MX/a/2015/010698, dated Jun. 15, 2018, 9 pages (English Translation).
Office Action in Mexican Patent Application No. MX/a/2017/001624, dated Jun. 25, 2019, 8 pages (with English Translation).
Office Action in Mexican Patent Application No. MX/a/2017/009892, dated Jul. 14, 2020, 7 pages (with English Translation).
Office Action in Mexican Patent Application No. MX/a/2018/006329, dated Jan. 19, 2021, 8 pages (with English Translation).
Office Action in Mexican Patent Application No. MX/a/2018/006329, dated Jul. 17, 2020, 6 pages (with English Translation).
Office Action in Mexican Patent Application No. MX/a/2018/006329, dated May 14, 2021, 5 pages (with English Translation).
Office Action in Mexican Patent Application No. MX/a/2020/002083, dated Jul. 21, 2022, 11 pages (with English Translation).
Office Action in Mexican Patent Application No. MX/a/2020/002083, dated May 12, 2022, 9 pages (with English Translation).
Office Action in Mexican Patent Application No. MX/a/2020/002083, dated Nov. 29, 2022, 11 pages (with English Translation).
Office Action in Mexican Patent Application No. MX/a/2020/008610, dated Apr. 12, 2022, 7 pages (with English Translation).
Office Action in New Zealand Patent Application No. 711101, dated May 1, 2018, 2 pages.
Office Action in Pakistani Patent Application No. 523/2016, dated May 3, 2018, 2 pages (English Translation).
Office Action in Pakistani Patent Application No. 94/2014, dated May 3, 2018, 2 pages (English Translation).
Office Action in Pakistani Patent Application No. 94/2014, dated May 13, 2016, 2 pages.
Office Action in Peruvian Patent Application No. 001748-2015, dated Apr. 19, 2019, 19 pages (with English Translation).
Office Action in Russian Patent Application No. 2015134558, dated Aug. 24, 2017, 11 pages (English Translation).

(56) References Cited

OTHER PUBLICATIONS

Office Action in Russian Patent Application No. 2015134558, dated Oct. 21, 2015, 3 pages (English Translation).
Office Action in Russian Patent Application No. 2017103439, dated Feb. 6, 2018, 6 pages (English Translation).
Office Action in Russian Patent Application No. 2017127135, dated Aug. 22, 2019, 16 pages (with English Translation).
Office Action in Russian Patent Application No. 2018119102, dated Feb. 4, 2020, 12 pages (with English Translation).
Office Action in Russian Patent Application No. 2020108284, dated May 17, 2022, 30 pages (with English Translation).
Office Action in Russian Patent Application No. 2020108284, dated Oct. 12, 2022, 11 pages (with English Translation).
Office Action in Russian Patent Application No. 2020108284, dated Oct. 27, 2021, 23 pages (with English Translation).
Office Action in Russian Patent Application No. 2020127993, dated Dec. 27, 2021, 21 pages (with English Translation).
Office Action in Singaporean Patent Application No. 11201700703X, dated Jun. 8, 2017, 5 pages (English Translation).
Office Action in Sri Lankan Patent Application No. 18355, dated Aug. 19, 2019, 1 page.
Office Action in Sri Lankan Patent Application No. 18355, dated Feb. 28, 2022, 1 page.
Office Action in Taiwanese Patent Application No. 103105419, dated May 14, 2018, 4 pages (English Translation).
Office Action in Taiwanese Patent Application No. 103105419, dated Oct. 24, 2017, 7 pages (English Translation).
Office Action in Thai Patent Application No. 1501004679, dated Jun. 11, 2018, 4 pages (English Translation).
Office Action in Thai Patent Application No. 1501004679, dated Sep. 26, 2017, 4 pages (English Translation).
Office Action in Ukrainian Patent Application No. a201508149, dated Aug. 11, 2017, 6 pages (English Translation).
Office Action in Ukrainian Patent Application No. a201508149, dated Oct. 6, 2015, 2 pages (English Translation).
Office Action in U.S. Appl. No. 14/183,864, dated Jun. 4, 2014, 7 pages.
Office Action in U.S. Appl. No. 14/183,864, dated Sep. 16, 2014, 7 pages.
Office Action in U.S. Appl. No. 15/500,429, dated Jul. 31, 2017, 8 pages.
Office Action in U.S. Appl. No. 15/547,139, dated Apr. 30, 2018, 26 pages.
Office Action in U.S. Appl. No. 15/771,193, dated Apr. 1, 2019, 5 pages.
Office Action in U.S. Appl. No. 15/771,193, dated Jun. 7, 2019, 44 pages.
Office Action in U.S. Appl. No. 15/771,193, dated Mar. 24, 2020, 12 pages.
Office Action in U.S. Appl. No. 15/774,193, dated Oct. 16, 2019, 44 pages.
Office Action in U.S. Appl. No. 16/225,722, dated Jul. 9, 2019, 33 pages.
Office Action in U.S. Appl. No. 16/642,105, dated Feb. 17, 2023, 24 pages.
Office Action in U.S. Appl. No. 16/642,105, dated Jul. 25, 2022, 17 pages.
Office Action in U.S. Appl. No. 16/642,105, dated Jun. 28, 2021, 65 pages.
Office Action in U.S. Appl. No. 16/642,105, dated Mar. 10, 2022, 25 pages.
Office Action in U.S. Appl. No. 16/642,105, dated Oct. 18, 2021, 19 pages.
Office Action in U.S. Appl. No. 16/970,683, dated Oct. 9, 2020, 29 pages.
Office Action in Vietnamese Patent Application No. 1-2015-02994, dated Jun. 21, 2017, 2 pages (English Translation).
Office Action in Vietnamese Patent Application No. 1-2015-02994, dated Sep. 30, 2015, 4 pages (English Translation).
Official Notification in Australian Patent Application No. 2019241625, dated Apr. 13, 2023, 1 page.
Official Notification in Australian Patent Application No. 2019241625, dated Jan. 4, 2023, 1 page.
Official Notification in Brazilian Patent Application No. BR112015019790-6, dated Jan. 21, 2020, 2 pages (with English Translation).
Official Notification in Brazilian Patent Application No. BR112015019790-6, dated Mar. 10, 2020, 4 pages (with English Translation).
Official Notification in Indian Patent Application No. 201847015401, dated Dec. 13, 2021, 21 pages.
Official Notification in U.S. Appl. No. 15/771,193, dated Aug. 10, 2020, 3 pages.
Official Notification in U.S. Appl. No. 16/970,683, dated May 10, 2022, 4 pages.
Patani and LaVoie, "Bioisosterism: A Rational Approach in Drug Design," Chem. Rev., 1996, 96:3147-3176.
Quintela-Fandino et al., "Nintedanib plus letrozole in early breast cancer: a phase 0/1 pharmacodynamic, pharmacokinetic, and safety clinical trial of combined FGFR1 and aromatase inhibition," Breast Cancer Research, 2019, 21:69.
Request to Amend Application Before Grant in Singapore Patent Application No. 11201506488W, dated Aug. 3, 2017, 21 pages (English Translation).
Response in Gulf Cooperation Council Patent Application No. GCC/P/2014/26467, dated Aug. 27, 2017, 18 pages (English Translation).
Response in Malaysian Patent Application No. PI2015702696, dated Nov. 6, 2017, 8 pages (English Translation).
Response in U.S. Appl. No. 15/500,429, dated Sep. 27, 2017, 6 pages.
Response in Vietnamese Patent Application No. 1-2015-02994, dated Aug. 7, 2017, 2 pages (English Translation).
Rubini et al., "Synthesis of Isosteric Methylene-Oxy Pseudodipeptide Analogues as Novel Amide Bond Surrogate Units", Tetrahedron, vol. 42, No. 21, 1986, p. 6039-p.6045.
Sasaki et al., "Increased FGFRI copy number in lung squamous cell carcinomas", Mol Med Report, 2012(5), p. 725-p. 728.
Seckl et al., "Radical trial: A phase Ib/IIa study to assess the safety and efficacy of AZD4547 in combination with either anastrozole or letrozole in ER positive breast cancer patients progressing on these aromatase inhibitors (AIs)," Journal of Clinical Oncology, 2017, 35(15):Supplement 1, 4 pages.
Seki et al., "Efficacy and Safety of Palbociclib and Fulvestrant in Japanese Patients With ER+/HER2− Advanced/Metastatic Breast Cancer," In Vivo, 2019, 33:2037-2044.
Shibata, "Clinical significance of Expression oFGFR2 Fusion Genes in Bile Duct Cancer", The Bilialy Tract & Pancreas, Feb. 12, 2015, vol. 36(2), p. 137-p. 142.
St. Bernard et al., "Fibroblast Growth Factor Receptors as Molecular Targets in Thyroid Carcinoma", Endocrinology, 2005(146), p. 1145-p. 1153.
Stahl et al., "Handbook of Pharmaceutical Salts Properties, Selection, and Use," 1st ed., Cover Page with Table of Contents, John Wiley & Sons, 2002, 4 pages.
Submission Document in Argentine Patent Application No. P140100495, dated Dec. 17, 2019, 7 pages (with English Translation).
Submission Document in Argentine Patent Application No. P140100495, dated Feb. 10, 2023, 8 pages (with English Translation).
Submission Document in Argentine Patent Application No. P140100495, dated Jan. 23, 2015, 7 pages (English Translation).
Submission Document in Australian Patent Application No. 2014219811, dated Aug. 22, 2017, 6 pages.
Submission Document in Australian Patent Application No. 2015304465, dated Apr. 5, 2019, 16 pages.
Submission Document in Australian Patent Application No. 2016237222, dated Jan. 19, 2021, 20 pages.
Submission Document in Australian Patent Application No. 2016237222, dated Mar. 22, 2021, 10 pages.
Submission Document in Australian Patent Application No. 2016374441, dated Sep. 22, 2021, 9 pages.

(56) References Cited

OTHER PUBLICATIONS

Submission Document in Brazilian Patent Application No. BR112015019790-6, dated Apr. 28, 2016, 19 pages (English Translation).
Submission Document in Brazilian Patent Application No. BR112015019790-6, dated Dec. 22, 2015, 12 pages (English Translation).
Submission Document in Brazilian Patent Application No. BR112015019790-6, dated Dec. 30, 2019, 16 pages (with English Translation).
Submission Document in Brazilian Patent Application No. BR1120170022680, dated Aug. 31, 2020, 21 pages (with English Translation).
Submission Document in Brazilian Patent Application No. BR1120170163926, dated Dec. 23, 2022, 18 pages (with English Translation).
Submission Document in Brazilian Patent Application No. BR1120170163926, dated Mar. 5, 2021, 19 pages (with English Translation).
Submission Document in Brazilian Patent Application No. BR1120170163926, dated Mar. 6, 2019, 16 pages (with English Translation).
Submission Document in Brazilian Patent Application No. BR1120180101036, dated Apr. 26, 2021, 20 pages (with English Translation).
Submission Document in Brazilian Patent Application No. BR1120200038490, dated Dec. 9, 2022, 37 pages (with English Translation).
Submission Document in Brazilian Patent Application No. BR1120200038490, dated Sep. 9, 2021, 51 pages (with English Translation).
Submission Document in Canadian Patent Application No. 2901585, dated Mar. 25, 2019, 42 pages.
Submission Document in Canadian Patent Application No. 2956270, dated Jan. 13, 2022, 5 pages.
Submission Document in Canadian Patent Application No. 2956270, dated Jun. 22, 2021, 26 pages.
Submission Document in Canadian Patent Application No. 2956270, dated Oct. 25, 2021, 7 pages.
Submission Document in Canadian Patent Application No. 2974937, dated Mar. 9, 2023, 8 pages.
Submission Document in Canadian Patent Application No. 3001969, dated Feb. 15, 2023, 7 pages.
Submission Document in Chilean Patent Application No. 2015-02311, dated Dec. 18, 2017, 40 pages (English Translation).
Submission Document in Chilean Patent Application No. 2015-02311, dated Jan. 8, 2016, 8 pages.
Submission Document in Chilean Patent Application No. 2015-02311, dated Jun. 13, 2017, 38 pages (English Translation).
Submission Document in Chinese Patent Application No. 201480009370.X, dated Feb. 25, 2016, 18 pages (English Translation).
Submission Document in Chinese Patent Application No. 201480009370.X, dated Mar. 21, 2017, 41 pages (English Translation).
Submission Document in Chinese Patent Application No. 201480009370.X, dated Oct. 10, 2016, 59 pages (English Translation).
Submission Document in Chinese Patent Application No. 201580042132.3, dated Oct. 22, 2018, 15 pages (with English Translation).
Submission Document in Chinese Patent Application No. 201680007472.7, dated Mar. 19, 2020, 8 pages (with English Translation).
Submission Document in Chinese Patent Application No. 201680007472.7, dated Oct. 10, 2019, 16 pages (with English Translation).
Submission Document in Chinese Patent Application No. 201680068110.9, dated Jul. 8, 2020, 8 pages.
Submission Document in Chinese Patent Application No. 201680068110.9, dated Mar. 1, 2021, 14 pages (with English Translation).
Submission Document in Chinese Patent Application No. 201680068110.9, dated Mar. 8, 2022, 40 pages (with English Translation).
Submission Document in Chinese Patent Application No. 201680068110.9, dated Oct. 8, 2018, 11 pages (English Translation).
Submission Document in Chinese Patent Application No. 201980013339.6, dated Feb. 3, 2023, 14 pages (with English Translation).
Submission Document in Chinese Patent Application No. 201980013339.6, dated Oct. 23, 2020, 6 pages (with English Translation).
Submission Document in Chinese Patent Application No. 202180028460.3, dated Dec. 21, 2023, 6 pages (with English Translation).
Submission Document in Chinese Patent Application No. 202180028460.3, dated Sep. 25, 2023, 31 pages (with English Translation).
Submission Document in Egyptian Patent Application No. PCT1285/2015, dated Aug. 19, 2015, 2 pages (English Translation).
Submission Document in Egyptian Patent Application No. PCT1285/2015, dated Jan. 4, 2022, 17 pages (with English Translation).
Submission Document in European Patent Application No. 14754294.8, dated Nov. 10, 2016, 9 pages.
Submission Document in European Patent Application No. 15834302.0, dated Dec. 3, 2021, 6 pages.
Submission Document in European Patent Application No. 15834302.0, dated Feb. 19, 2020, 74 pages.
Submission Document in European Patent Application No. 15834302.0, dated Oct. 2, 2018, 80 pages.
Submission Document in European Patent Application No. 15834302.0, dated Sep. 14, 2021, 75 pages.
Submission Document in European Patent Application No. 16768810.0, dated Feb. 11, 2019, 9 pages.
Submission Document in European Patent Application No. 16768810.0, dated Sep. 30, 2020, 5 pages.
Submission Document in European Patent Application No. 18865416.4, dated Dec. 16, 2021, 13 pages.
Submission Document in European Patent Application No. 18865416.4, dated Jul. 29, 2020, 11 pages.
Submission Document in European Patent Application No. 19777797.2, dated May 2, 2022, 18 pages.
Submission Document in Indian Patent Application No. 201747003469, dated Feb. 9, 2021, 8 pages.
Submission Document in Indian Patent Application No. 201747003469, dated Jan. 13, 2020, 12 pages.
Submission Document in Indian Patent Application No. 201747027065, dated Aug. 18, 2020, 6 pages.
Submission Document in Indian Patent Application No. 201747027065, dated May 21, 2020, 23 pages.
Submission Document in Indian Patent Application No. 201847015401, dated Aug. 11, 2021, 6 pages.
Submission Document in Indian Patent Application No. 201847015401, dated Mar. 10, 2022, 16 pages.
Submission Document in Indian Patent Application No. 201847015401, dated Oct. 18, 2022, 3 pages.
Submission Document in Indian Patent Application No. 201847015401, dated Oct. 29, 2020, 20 pages.
Submission Document in Indian Patent Application No. 202047007881, dated May 11, 2022, 13 pages.
Submission Document in Indian Patent Application No. 202047036696, dated Jul. 15, 2022, 11 pages.
Submission Document in Indian Patent Application No. 4989/CHENP/2015, dated Apr. 15, 2019, 24 pages.
Submission Document in Indian Patent Application No. 4989/CHENP/2015, dated May 9, 2016, 7 pages (English Translation).
Submission Document in Indonesian Patent Application No. P-00201505035, dated Apr. 26, 2019, 8 pages (with English Translation).

(56) References Cited

OTHER PUBLICATIONS

Submission Document in Indonesian Patent Application No. P-00201505035, dated Apr. 27, 2016, 10 pages (English Translation).
Submission Document in Indonesian Patent Application No. P-00201505035, dated Dec. 5, 2016, 3 pages.
Submission Document in Israeli Patent Application No. 240623, dated Apr. 16, 2018, 15 pages (English Translation).
Submission Document in Israeli Patent Application No. 240623, dated May 18, 2016, 3 pages (English Translation).
Submission Document in Israeli Patent Application No. 250290, dated Apr. 13, 2020, 6 pages (with English Translation).
Submission Document in Israeli Patent Application No. 250290, dated Dec. 26, 2018, 4 pages.
Submission Document in Israeli Patent Application No. 250290, dated Nov. 28, 2019, 8 pages (with English Translation).
Submission Document in Israeli Patent Application No. 253701, dated Feb. 4, 2019, 8 pages (English Translation).
Submission Document in Israeli Patent Application No. 253701, dated Feb. 5, 2020, 7 pages (with English Translation).
Submission Document in Israeli Patent Application No. 258671, dated Aug. 3, 2021, 4 pages (with English Translation).
Submission Document in Israeli Patent Application No. 258671, dated Jul. 25, 2022, 24 pages.
Submission Document in Israeli Patent Application No. 258671, dated Nov. 26, 2019, 4 pages (with English Translation).
Submission Document in Israeli Patent Application No. 258671, dated Sep. 30, 2020, 35 pages (with English Translation).
Submission Document in Israeli Patent Application No. 272887, dated Mar. 16, 2021, 7 pages (with English Translation).
Submission Document in Israeli Patent Application No. 276935, dated Jul. 13, 2021, 4 pages (with English Translation).
Submission Document in Japanese Patent Application No. P2014-526292, dated May 30, 2014, 14 pages (English Translation).
Submission Document in Japanese Patent Application No. P2015-560425, dated Mar. 24, 2016, 8 pages (English Translation).
Submission Document in Japanese Patent Application No. P2017-508383, dated Feb. 8, 2019, 80 pages (English Translation).
Submission Document in Japanese Patent Application No. P2020-510951, dated Feb. 28, 2023, 15 pages (with English Translation).
Submission Document in Jordanian Patent Application No. 39/2014, dated Mar. 15, 2018, 12 pages (English Translation).
Submission Document in Korean Patent Application No. 10-2015-7022252, dated Oct. 25, 2019, 43 pages (with English Translation).
Submission Document in Korean Patent Application No. 10-2017-7002791, dated Oct. 8, 2021, 23 pages (with English Translation).
Submission Document in Korean Patent Application No. 10-2017-7021185, dated Apr. 3, 2023, 18 pages (with English translation).
Submission Document in Korean Patent Application No. 10-2020-7005278, dated Jul. 29, 2021, 12 pages (with English Translation).
Submission Document in Malaysian Patent Application No. PI 2015702696, dated Apr. 7, 2016, 4 pages.
Submission Document in Malaysian Patent Application No. PI 2015702696, dated Jan. 6, 2016, 207 pages.
Submission Document in Mexican Patent Application No. MX/a/2015/010698, dated Aug. 2, 2018, 17 pages (English Translation).
Submission Document in Mexican Patent Application No. MX/a/2017/001624, dated Aug. 21, 2019, 11 pages (with English Translation).
Submission Document in Mexican Patent Application No. MX/a/2018/006329, dated Mar. 11, 2021, 9 pages (with English Translation).
Submission Document in Mexican Patent Application No. MX/a/2018/006329, dated Oct. 8, 2020, 7 pages (with English Translation).
Submission Document in Mexican Patent Application No. MX/a/2020/002083, dated Jul. 11, 2022, 21 pages (with English Translation).
Submission Document in Mexican Patent Application No. MX/a/2020/002083, dated Sep. 22, 2022, 2 pages (with English Translation).
Submission Document in Mexican Patent Application No. MX/a/2020/008610, dated Jun. 15, 2022, 7 pages (with English Translation).
Submission Document in New Zealand Patent Application No. 711101, dated Apr. 12, 2016, 9 pages.
Submission Document in New Zealand Patent Application No. 711101, dated Jan. 20, 2016, 5 pages.
Submission Document in New Zealand Patent Application No. 711101, dated Jul. 20, 2018, 6 pages.
Submission Document in Pakistani Patent Application No. 523/2016, dated Jun. 4, 2018, 1 page (English Translation).
Submission Document in Pakistani Patent Application No. 94/2014, dated Aug. 25, 2016, 14 pages.
Submission Document in Pakistani Patent Application No. 94/2014, dated Jul. 7, 2018, 4 pages.
Submission Document in Peruvian Patent Application No. 001748-2015, dated Dec. 21, 2015, 9 pages (English Translation).
Submission Document in Peruvian Patent Application No. 001748-2015, dated Jul. 6, 2019, 6 pages (with English Translation).
Submission Document in Peruvian Patent Application No. 001748-2015, dated Jun. 21, 2019, 4 pages (with English Translation).
Submission Document in Philippine Patent Application No. 1-2015-501813, dated Apr. 4, 2016, 1 page (English Translation).
Submission Document in Philippine Patent Application No. 1-2015-501813, dated Dec. 21, 2015, 3 pages (English Translation).
Submission Document in Russian Patent Application No. 2015134558, dated Apr. 22, 2016, 14 pages (English Translation).
Submission Document in Russian Patent Application No. 2015134558, dated Dec. 25, 2015, 16 pages.
Submission Document in Russian Patent Application No. 2015134558, dated Nov. 22, 2017, 21 pages (English Translation).
Submission Document in Russian Patent Application No. 2017103439, dated Mar. 20, 2018, 19 pages (English Translation).
Submission Document in Russian Patent Application No. 2017127135, dated Nov. 14, 2019, 21 pages (with English Translation).
Submission Document in Russian Patent Application No. 2018119102, dated Apr. 27, 2020, 14 pages (with English Translation).
Submission Document in Russian Patent Application No. 2020108284, dated Aug. 10, 2022, 11 pages (with English Translation).
Submission Document in Russian Patent Application No. 2020108284, dated Mar. 17, 2022, 16 pages (with English Translation).
Submission Document in Russian Patent Application No. 2020127993, dated Mar. 11, 2022, 9 pages (with English Translation).
Submission Document in Singaporean Patent Application No. 10201913213W, dated Dec. 1, 2022, 8 pages.
Submission Document in Singaporean Patent Application No. 11201506488W, dated Dec. 23, 2015, 5 pages.
Submission Document in Singaporean Patent Application No. 11201700703X, dated Jul. 19, 2017, 16 pages (English Translation).
Submission Document in Singaporean Patent Application No. 11201706143S, dated May 30, 2019, 13 pages.
Submission Document in Sri Lankan Patent Application No. 18355, dated Nov. 14, 2022, 2 pages.
Submission Document in Sri Lankan Patent Application No. 18355, dated Nov. 21, 2019, 3 pages.
Submission Document in Taiwanese Patent Application No. 103105419, dated Aug. 8, 2018, 19 pages (English Translation).
Submission Document in Taiwanese Patent Application No. 103105419, dated Jan. 23, 2018, 30 pages (English Translation).
Submission Document in Thai Patent Application No. 1501004679, dated Jul. 20, 2018, 4 pages (English Translation).
Submission Document in Thai Patent Application No. 1501004679, dated Nov. 20, 2017, 6 pages (English Translation).
Submission Document in Ukrainian Patent Application No. a201508149, dated Nov. 20, 2017, 20 pages (English Translation).
Submission Document in Ukrainian Patent Application No. a201508149, dated Oct. 6, 2015, 4 pages (English Translation).
Submission Document in U.S. Appl. No. 15/547,139, dated Apr. 30, 2019, 11 pages.

(56) References Cited

OTHER PUBLICATIONS

Submission Document in U.S. Appl. No. 15/547,139, dated Dec. 17, 2018, 5 pages.
Submission Document in U.S. Appl. No. 15/547,139, dated Jul. 25, 2018, 13 pages.
Submission Document in U.S. Appl. No. 15/771,193, dated Aug. 22, 2019, 9 pages.
Submission Document in U.S. Appl. No. 15/771,193, dated Aug. 9, 2021, 5 pages.
Submission Document in U.S. Appl. No. 15/771,193, dated Dec. 18, 2023, 8 pages.
Submission Document in U.S. Appl. No. 15/771,193, dated Jan. 16, 2020, 20 pages.
Submission Document in U.S. Appl. No. 15/771,193, dated Jan. 21, 2021, 12 pages.
Submission Document in U.S. Appl. No. 15/771,193, dated Jan. 25, 2023, 5 pages.
Submission Document in U.S. Appl. No. 15/771,193, dated Jun. 23, 2022, 5 pages.
Submission Document in U.S. Appl. No. 15/771,193, dated Mar. 7, 2022, 5 pages.
Submission Document in U.S. Appl. No. 15/771,193, dated May 14, 2019, 8 pages.
Submission Document in U.S. Appl. No. 15/771,193, dated May 16, 2023, 5 pages.
Submission Document in U.S. Appl. No. 15/771,193, dated May 3, 2021, 5 pages.
Submission Document in U.S. Appl. No. 15/771,193, dated Nov. 22, 2021, 5 pages.
Submission Document in U.S. Appl. No. 15/771,193, dated Oct. 5, 2022, 5 pages.
Submission Document in U.S. Appl. No. 15/771,193, dated Sep. 13, 2023, 9 pages.
Submission Document in U.S. Appl. No. 16/225,772, dated Dec. 19, 2018, 104 pages.
Submission Document in U.S. Appl. No. 16/225,772, dated Oct. 21, 2020, 5 pages.
Submission Document in U.S. Appl. No. 16/225,772, dated Sep. 30, 2019, 10 pages.
Submission Document in U.S. Appl. No. 16/642,105, dated Jan. 5, 2022, 17 pages.
Submission Document in U.S. Appl. No. 16/642,105, dated Jun. 7, 2022, 10 pages.
Submission Document in U.S. Appl. No. 16/642,105, dated Jun. 8, 2020, 99 pages.
Submission Document in U.S. Appl. No. 16/642,105, dated Oct. 25, 2022, 17 pages.
Submission Document in U.S. Appl. No. 16/642,105, dated Sep. 15, 2021, 7 pages.
Submission Document in U.S. Appl. No. 16/970,683, dated Apr. 9, 2021, 5 pages.
Submission Document in U.S. Appl. No. 16/970,683, dated Dec. 23, 2020, 22 pages.
Submission Document in U.S. Appl. No. 16/970,683, dated Jul. 14, 2021, 5 pages.
Submission Document in U.S. Appl. No. 16/970,683, dated Oct. 28, 2021, 5 pages.
Submission Document in Vietnamese Patent Application No. 1-2015-02994, dated May 25, 2016, 12 pages (English Translation).
Submission Document in Vietnamese Patent Application No. 1-2015-02994, dated Oct. 28, 2015, 22 pages (English Translation).
Tsimafeyeu et al., "Overexpression of fibroblast growth factor receptors FGFR1 and FGFR2 in renal cell carcinoma", Scand J Urol Nephrol, 2011(45), p. 190-p. 195.
Tsuruoka et al., "Preclinical and clinical researches of lenvatinib mesylate (Lenvima capsule), a novel antitumor agent approved for thyroid cancer treatment," Folia Pharmacologica Japonica, 2015, 146:283-290 (with English Abstract).
Tsuruoka et al., "Preclinical and clinical researches of lenvatinib mesylate (Lenvima capsule), a novel antitumor agent approved for thyroid cancer treatment," Folia Pharmacologica Japonica, 2015, 146:283-290 (with English Translation).
Turner et al., "FGFRI Amplification Drives Endocrine Therapy Resistance and Is a Therapeutic Target in Breast Cancer," Cancer Research, vol. 70, No. 5, Mar. 1, 2010, p. 2085-p. 2094.
Turner et al., "Fibroblast growth factor signaling: from development to cancer", Nature Reviews Cancer, 2010 vol. 10, p. 116-p. 129.
Wang et al., "Downregulation of microRNA-214 and overexpression of FGFR-1 contribute to hepatocellular carcinoma metastasis," Biochemical and Biophysical Research Communications, 2013, 439(1):47-53.
Watanabe et al., "Abstract 770: E7090: A potent and selective FGFR inhibitor with activity in multiple FGFR-driven cancer models with distinct mechanisms of activation," Cancer Research, 2015, 75(Suppl. 15):1-4, XP002792860 (Abstract Only).
Watanabe Miyano et al., "E7090, a Novel Selective Inhibitor of Fibroblast Growth Factor Receptors, Displays Potent Antitumor Activity and Prolongs Survival in Preclinical Models," Molecular Cancer Therapeutics, vol. 15, No. 11, 2016.11, p. 2630-p. 2639.
Weiss et al., "Frequent and Focal FGFR1 Amplification Associates with Therapeutically Tractable FGFR1 Dependency in Squamous Cell Lung Cancer", Sci Transl Med, Apr. 18, 2012, p. 1-p. 7.
Wesche et al., "Fibroblast growth factors and their receptors in cancer", Biochem J., 2011(437), p. 199-p. 213.
Wu et al., "Identification of Targetable FGFR Gene Fusions in Diverse Cancers," Cancer Discovery, 2013 American Association for Cancer, Research Brief, 2013, 13 pages.
Ye et al., "Expression and Significance of FGFR2 in Colon Cancer," China Modern Doctor, 2012, 50(5):1-3 (with English Translation).
Yin et al., "A General and Efficient 2-Amination of Pyridines and Quinolines," Journal of Organic Chemistry, 2007, 72(12):4554-4557.
Yu et al., "A FGFR1 inhibitor patent review: progress since 2010," Expert Opinion on Therapeutic Patents, 2016, pp. 1-16, XP055339480.
Zhang et al., "Translating the Therapeutic Potential of AZD4547 in FGFR1-Amplified Non-Small Cell Lung Cancer through the Use of Patient-Derived Tumor Xenograft Models", Clinical Cancer Research, May 24, 2013, p. 6657-p. 6667.
Zhou et al., "CDK4/6 inhibitor resistance in estrogen receptor positive breast cancer, a 2023 perspective," Frontiers in Cell and Developmental Biology, Mar. 22, 2023, 11:1-12.
Submission Document in U.S. Appl. No. 15/771,193, dated Jul. 3, 2024, 11 pages.
Notice of Allowance in U.S. Appl. No. 15/547,139, dated Nov. 19, 2024, 8 pages.
Office Action in Israeli Patent Application No. 310339, dated Nov. 25, 2024, 5 pages (with English translation).
Office Action in Russian Patent Application No. 2024102255, dated Dec. 26, 2025, 9 pages (with English translation).
Reexamination Decision for Chinese Patent Application No. 202210570963.X, dated Jan. 5, 2026, 17 pages (with English translation).
Notice of Allowance in Russian Patent Application No. 2022127618, dated Aug. 18, 2025, 16 pages (with English translation).
Office Action in Chinese Patent Application No. 202210570963.X, dated Aug. 19, 2025, 10 pages (with English translation).
Office Action in Russian Patent Application No. 2022134723, dated Aug. 8, 2025, 25 pages (with English translation).
Submission Document in European Patent Application No. 22864456.3, dated Aug. 25, 2025, 15 pages.
Tallarida, "Quantitative Methods for Assessing Drug Synergism," Genes & Cancer, 2011, 2(11):1003-1008.
Notice of Allowance in U.S. Appl. No. 15/771,193, dated Feb. 4, 2025, 12 pages.
Submission Document in Israeli Patent Application No. 310338, dated Mar. 18, 2025, 5 pages (with English Translation).
Cancer.gov [online], "Tumor List," National Cancer Institute SEER Training Modules, retrieved on Feb. 13, 2026, retrieved from URL <https://training.seer.cancer.gov/disease/categories/tumors.html>, 5 pages.
El-Sayes et al., "Tumor Heterogeneity: A Great Barrier in the Age of Cancer Immunotherapy," Cancers, Feb. 15, 2021, 13(4):806, 14 pages.

(56) References Cited

OTHER PUBLICATIONS

Hanahan et al., "The Hallmarks of Cancer," Cell, Jan. 7, 2000, 100(1):57-70.
HopkinsMedicine.org [online], "Brain Tumor Types," Johns Hopkins Medicine, retrieved on Feb. 13, 2026, retrieved from URL <https://www.hopkinsmedicine.org/health/conditions-and-diseases/brain-tumor/brain- tumor-types>, 9 pages.
Khasraw et al., "PD-1 Inhibitors: Do they have a Future in the Treatment of Glioblastoma?," Clinical Cancer Research, Oct. 15, 2020, 26(20):5287-5296.
Marino et al., "Molecular heterogeneity in lung cancer: from mechanisms of origin to clinical implications," International Journal of Medical Sciences, Jun. 10, 2019, 16(7):981-989.
Mason-Osann et al., "Synergistic Drug Combinations Promote the Development of Resistance in Acute Myeloid Leukemia," Blood Cancer Discovery, Mar. 2024, 5(2):95-105.
Office Action in U.S. Appl. No. 18/030,207, dated Mar. 25, 2026, 217 pages.
Restriction Requirement in U.S. Appl. No. 18/292,743, dated Mar. 10, 2026, 6 pages.
Rivenbark et al., "Molecular and Cellular Heterogeneity in Breast Cancer: Challenges for Personalized Medicine," The American Journal of Pathology, Oct. 2013, 183(4):1113-1124.
Submission Document in Canadian Patent Application No. 3180128, dated Mar. 23, 2026, 12 pages.
Submission Document in Chinese Patent Application No. 202180072012.3, dated Mar. 12, 2026, 19 pages (with English translation)
Submission Document in European Patent Application No. 21787967.5, dated Mar. 12, 2026, 29 pages (with enclosures).
Submission Document in European Patent Application No. 21850938.8, dated Mar. 19, 2026, 9 pages.
Submission Document in Taiwanese Patent Application No. 111132531, dated Mar. 3, 2026, 17 pages (with English translation).
Sun et al., "Resistance to PD-1/PD-L1 blockade cancer immunotherapy: mechanisms, predictive factors, and future perspectives," Biomarker Research, Aug. 26, 2020, 8(1):35, 10 pages.
European Search Report in European Patent Application No. 22864455.5, dated Jul. 21, 2025, 13 pages.
Submission Document in Taiwanese Patent Application No. 110139617, dated Jul. 7, 2025, 20 pages (with English translation).
Office Action in Korean Patent Application No. 10-2020-7024300, dated Jul. 15, 2024, 8 pages (with English Translation).
Notice of Allowance in U.S. Appl. No. 15/547,139, dated, Jun. 18, 2024, 8 pages.
Submission Document in U.S. Appl. No. 18/008,304, dated Nov. 10, 2025, 18 pages.
Office Action in Chinese Patent Application No. 202180045666.7, dated Jul. 31, 2024, 23 pages (with English Translation).
Notice of Allowance in Mexican Patent Application No. MX/a/2022/012934, dated Aug. 25, 2025, 6 pages (with English translation).
Notice of Allowance in U.S. Appl. No. 15/771,193, dated Nov. 6, 2024, 11 pages.
Submission Document in Russian Patent Application No. 2022127618, dated Oct. 10, 2024, 23 pages (with English Translation).
Submission Document in U.S. Appl. No. 15/771,193, dated Oct. 25, 2024, 8 pages.
Notice of Allowance in U.S. Appl. No. 16/225,772, dated Nov. 15, 2024, 8 pages.
Cui et al., "Comparative effectiveness of pembrolizumab vs. nivolumab in patients with recurrent or advanced NSCLC," Scientific Reports, Aug. 4, 2020, 10:13160, 7 pages.
International Search Report and Written Opinion in International Application No. PCT/JP2025/022823, dated Aug. 26, 2025, 11 pages.
Karkera et al., "Oncogenic Characterization and Pharmacologic Sensitivity of Activating Fibroblast Growth Factor Receptor (FGFR) Genetic Alterations to the Selective FGFR Inhibitor Erdafitinib," Mol. Cancer Ther., Aug. 2017, 16(8):1717-1726.
Kim et al., "Co-clinical trials demonstrate predictive biomarkers for dovitinib, an FGFR inhibitor, in lung squamous cell carcinoma," Annals of Oncology, Jun. 2017, 28(6):1250-1259.
Office Action in Japanese Patent Application No. P2022-559159, dated Mar. 24, 2026, 11 pages (with English translation).
Palakurthi et al., "The combined effect of FGFR inhibition and PD-1 blockade promotes tumor-intrinsic induction of antitumor immunity," Cancer Immunology Research, Sep. 2019, 7(9):1457-1471.
Submission Document in Taiwanese Patent Application No. 111132533, dated Mar. 12, 2026, 19 pages (with English translation).
Zhao et al., "Comparisons of Underlying Mechanisms, Clinical Efficacy and Safety Between Anti-PD-1 and Anti-PD-L1 Immunotherapy: The State-of-the-Art Review and Future Perspectives," Frontiers in Pharmacology, Jul. 7, 2021, 12:714483, 13 pages.
Submission Document in Russian Patent Application No. 2022127618, dated Feb. 4, 2025, 5 pages (with English Translation).
Office Action in Russian Patent Application No. 2022127618, dated Apr. 3, 2025, 15 pages (with English Translation).
Office Action in Japanese Patent Application No. 2022-515429, dated Jan. 14, 2025, 6 pages (with English translation).
Office Action in Singaporean Patent Application No. 10201913213W, dated Jan. 14, 2025, 8 pages.
Submission Document in Chinese Patent Application No. 202210570963.X, dated Feb. 5, 2025, 9 pages (with English Translation).
Notice of Allowance in U.S. Appl. No. 15/547,139, dated Mar. 18, 2025, 12 pages.
Submission Document in Israeli Patent Application No. 310339, dated Mar. 20, 2025, 5 pages (with English Translation).
Office Action in Japanese Patent Application No. P2023-086361, dated Feb. 24, 2026, 8 pages (with English translation).
Office Action in Japanese Patent Application No. P2023-086373, dated Feb. 24, 2026, 10 pages (with English translation).
Office Action in Japanese Patent Application No. P2022-559159, dated Oct. 28, 2025, 7 pages (with English translation).
Submission Document in Japanese Patent Application No. P2022-515429, dated Oct. 7, 2025, 12 pages (with English translation).
Murakami, "Development of Commercial Manufacturing Method for Fibroblast Growth Factor Receptor(FGFR1,FGFR2 and FGFR3)Selective Tyrosine Kinase Inhibitor, Tasurgratinib Succinate," Presented at Pacifichem 2025, Dec. 15-20, 2025, Honolulu, Hawaii, 37 pages.
Office Action in Korean Patent Application No. 10-2022-7045161, dated Dec. 9, 2025, 12 pages (with English translation).
Office Action in Taiwanese Patent Application No. 111132531, dated Dec. 5, 2025, 9 pages (with English translation).
Office Action in Taiwanese Patent Application No. 111132533, dated Dec. 17, 2025, 15 pages (with English translation).
Office Action in Russian Patent Application No. 2022127618, dated Aug. 14, 2024, 37 pages (with English Translation).
Notice of Allowance in Thai Patent Application No. 1501004679, dated Oct. 31, 2024, 2 pages (with English Translation).
Notice of Allowance in U.S. Appl. No. 15/547,139, dated Nov. 6, 2024, 21 pages.
Submission Document in Chinese Patent Application No. 202180045666.7, dated Nov. 19, 2024, 61 pages (with English Translation).
Office Action in European Patent Application No. 21787967.5, dated Nov. 19, 2025, 9 pages.
Office Action in European Patent Application No. 21850938.8, dated Nov. 19, 2025, 8 pages.
Office Action in Korean Patent Application No. 10-2022-7039422, dated Nov. 17, 2025, 11 pages (with English translation).
Kharkevich, "FARMAKOLOGIA [Pharmacology]," Moscow: GEOTAR-Media, 10th Edition, 2010, pp. 76-77 (with English Translation).
Komarov et al., "The use of Aromatase Inhibitors in Hormone Full Therapy of Patients with Breast Cancer," Federal State Budgetary Scientific Institution, N. N. Blokhin National Medical Research Center of Oncology, Ministry of Health of Russia, 2016, pp. 17-25 (with English Translation).

(56) References Cited

OTHER PUBLICATIONS

Office Action in Russian Patent Application No. 2022134723, dated Nov. 2, 2024, 34 pages (with English Translation).
Polyanskikh et al., "Current Understanding of Selective Estrogen Receptor Modulators," Journal of Obstetrics and Women's Diseases, 2019, 68(6):99-106 (with English Translation).
Submission Document in Russian Patent Application No. 2022134723, dated Jan. 6, 2025, 25 pages (with English Translation).
Tentsova, "Spravochnik Farmatsevta [Pharmacist's Reference Manual]," Corresponding Member of the Academy of Medical Sciences of the USSR, Moscow "Medicine," Second edition, revised and expanded, 1981, pp. 150-151 (with English Translation).
Notice of Allowance in U.S. Appl. No. 15/547,139, dated Mar. 27, 2025, 12 pages.
Office Action in Japanese Patent Application No. P2022-515429, dated Apr. 22, 2025, 13 pages (with English Translation).
Office Action in Taiwanese Patent Application No. 110127880, dated Apr. 10, 2025, 29 pages (with English Translation).
Office Action in Taiwanese Patent Application No. 110139617, dated Apr. 15, 2025, 8 pages (with English Translation).
Notice of Allowance in U.S. Appl. No. 15/771,193, dated Aug. 21, 2024, 4 pages.
Submission Document in European Patent Application No. 22864455.5, dated Dec. 11, 2025, 11 pages.
Office Action in Indian Patent Application No. 202247065581, dated Feb. 19, 2026, 8 pages.
Office Action in Chinese Patent Application No. 202210570963.X, dated Oct. 18, 2024, 12 pages (with English Translation).
Notice of Allowance in U.S. Appl. No. 15/771,193, dated Jul. 26, 2024, 12 pages.
Kharkevich, "Pharmacology," Moscow: GEOTAR-Media, 10th Edition, 2010, pp. 73-74 (with English Translation).
Office Action in Russian Patent Application No. 2022127618, dated Dec. 10, 2024, 16 pages (with English Translation).
Submission Document in U.S. Appl. No. 15/771,193, dated Jan. 16, 2025, 8 pages.
Zhulenko et al., "Pharmacology," Moscow: KolosS, 2008, pp. 34-35 (with English Translation).
Notice of Allowance in U.S. Appl. No. 16/225,772, dated Feb. 14, 2025, 6 pages.
Submission Document in European Patent Application No. 21886203.5, dated Feb. 21, 2025, 12 pages.
Submission Document in Russian Patent Application No. 2024102255, dated Feb. 17, 2026, 11 pages (with English translation).
Office Action in Japanese Patent Application No. 2022-539547, dated Jun. 17, 2025, 12 pages (with English Translation).
Submission Document in Chinese Patent Application No. 202180045666.7, dated Jun. 24, 2025, 20 pages (with English Translation).
Office Action in Israeli Patent Application No. 310338, dated Nov. 25, 2024, 5 pages (with English translation).

PRODUCTION METHOD FOR SYNTHETIC INTERMEDIATE OF MONOCYCLIC PYRIDINE DERIVATIVE

TECHNICAL FIELD

The present invention relates to a method for producing synthesis intermediates of monocyclic pyridine derivatives that are useful as FGFR inhibitors.

BACKGROUND ART

The monocyclic pyridine derivative 5-((2-(4-(1-(2-hydroxyethyl)piperidin-4-yl)benzamide)pyridin-4-yl)oxy)-6-(2-methoxyethoxy)-N-methyl-1H-indole-1-carboxamide butanedioate (2:3)

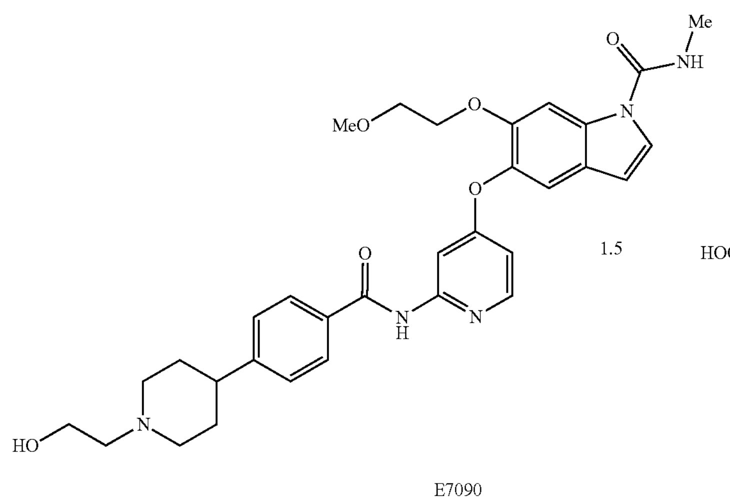

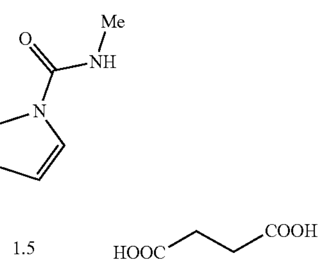

E7090

(hereunder also referred to as "E7090") has potent FGFR (Fibroblast Growth Factor Receptor) inhibitory action and is useful as a therapeutic agent for FGFR kinase-associated intrahepatic cholangiocarcinoma and breast cancer (PTLs 1 and 2).

CITATION LIST

Patent Literature

[PTL 1] International Patent Publication No. WO2014/129477

[PTL 2] International Patent Publication No. WO2016/027781

SUMMARY OF INVENTION

Technical Problem

Methods for producing important intermediates of E7090 are described in PTL 1 (Examples 20 and 22) and PTL 2 (Example 1).

Compound (1g) in PTL 1 is synthesized by reacting 1-bromo-3-methoxypropane with 3,4-dihydroxybenzaldehyde (compound (P 1-1)), but the selectivity for alkylation of the phenolic hydroxyl group is low, while highly toxic and hazardous nitromethane is used for conversion from compound (P 1-3) to compound (P 1-4), and compound (P 1-5) obtained by nitration of compound (P 1-4) is an explosive compound. Moreover, the steps for converting compound (P 1-3) to compound (P 1-5) via compound (P 1-4) are all highly dangerous. It has therefore been desirable to devise a new, safe and efficient route of synthesis that produces higher yield.

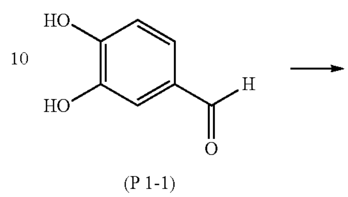

(P 1-1)

-continued

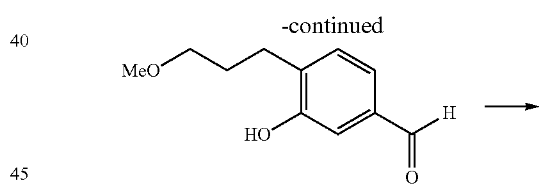

(P 1-2)

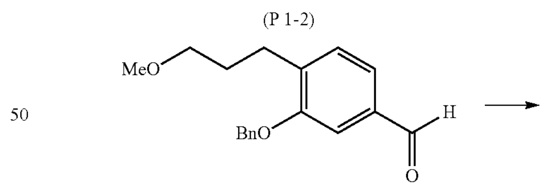

(P 1-3)

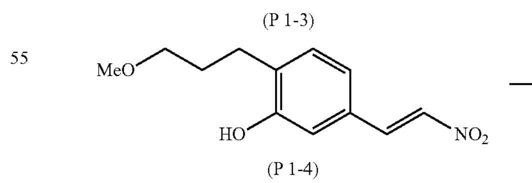

(P 1-4)

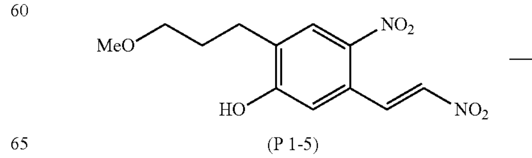

(P 1-5)

-continued

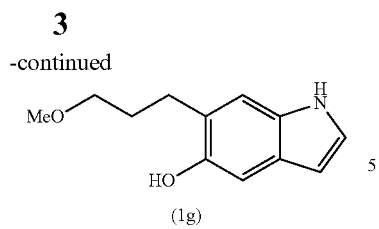

(1g)

Compound (2i) described in PTL 1 is synthesized by reacting 4-chloropyridine (compound (P 2-1)) with compound (1g) in the presence of a base, but the yield of the target compound (P 2-2) has been low since N,O-diallylated products are also produced in addition to compound (P 2-2), due to allylation of the indole nitrogen atom together with the phenolic hydroxyl group. The reaction also requires a high temperature of 150° C. or above, and therefore a method has been sought for constructing heterobiaryl backbones under mild conditions.

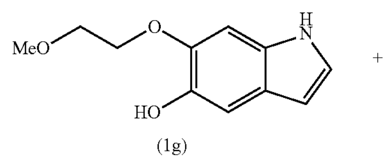

(1g)

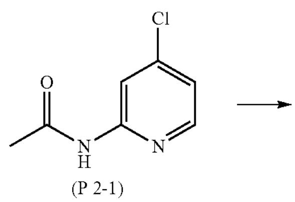

(P 2-1)

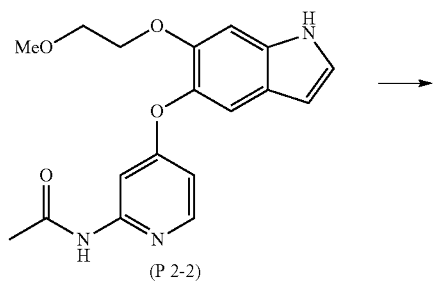

(P 2-2)

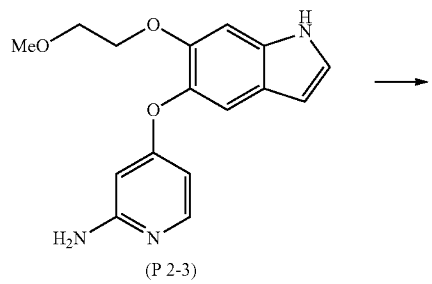

(P 2-3)

-continued

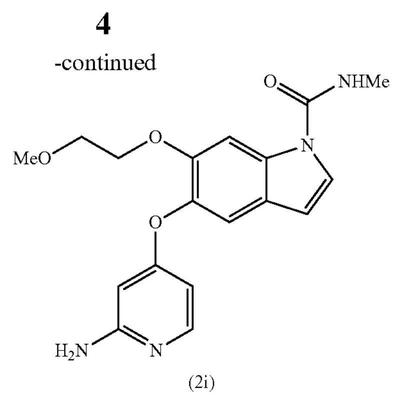

(2i)

It is an object of the present application to provide a production process allowing high-yield and efficient synthesis of key intermediates for production of E7090, which is useful as an FGFR inhibitor.

Solution to Problem

Provided herein are synthesis intermediates that are useful for production of E7090, which is useful as an FGFR inhibitor, as well as a process for their production. Specifically, the present invention provides the following [1] to [7].

[1] A process for producing compound (2i):

(2i)

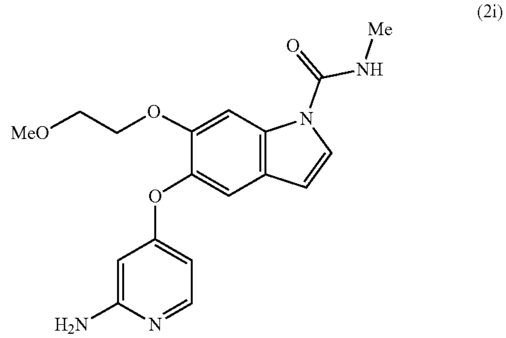 [SMILES: CNC(=O)n1ccc2cc(Oc3ccnc(N)c3)c(OCCOC)cc21]

or a salt thereof, wherein the process comprises:

2-a) step 2-a) in which a protecting group is introduced into compound (1g):

(1g)

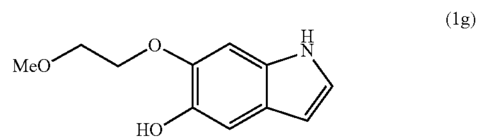 [SMILES: COCCOc1cc2[nH]ccc2cc1O]

to produce compound (2a):

(2a)

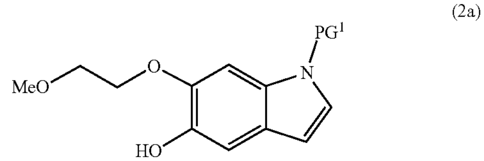

(where $PG^1$ represents a nitrogen protecting group), 2-b) step 2-b) in which compound (2a) obtained in step 2-a) and compound (2b):

(2b)

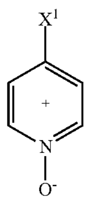

(where $X^1$ represents a leaving group), are reacted in the presence of a base to produce compound (2c):

(2c)

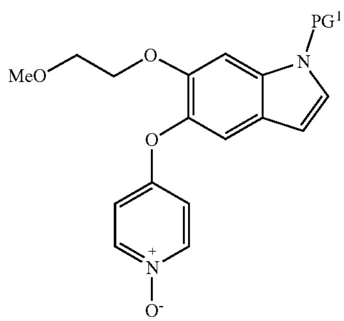

(where $PG^1$ represents the same group as specified above), 2-c) step 2-c) in which compound (2c) obtained in step 2-b) and compound (2d):

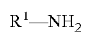 (2d)

(where $R^1$ represents a tert-pentyl, tert-butyl, tert-octyl or cumyl group), are reacted in the presence of an activating agent to produce compound (2e):

(2e)

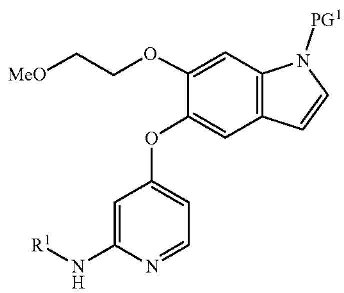

(where $PG^1$ and $R^1$ each represent the same groups as specified above), 2-d) step 2-d) in which $PG^1$ in compound (2e) obtained in step 2-c) is removed to produce compound (2f):

(2f)

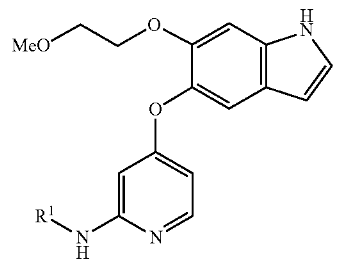

(where $R^1$ represents the same group as specified above), 2-e) step 2-e) in which compound (2f) obtained in step 2-d) and compound (2g-1) or compound (2g-2):

(2g-1)

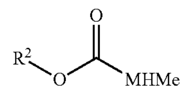

(2g-2)

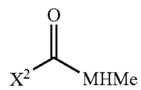

(where $R^2$ of formula (2g-1) is a $C_{1-6}$ alkyl group or $C_{6-10}$ aryl group, the $C_{1-6}$ alkyl group optionally having 1 to 3 identical or different substituents selected from the group consisting of halogen atoms and methoxy groups, and the $C_{6-10}$ aryl group optionally having 1 to 3 identical or different substituents selected from halogen atoms and methyl, methoxy and nitro groups, and $X^2$ of formula (2g-2) represents a halogen atom), are reacted in the presence of a base to produce compound (2h):

(2h)

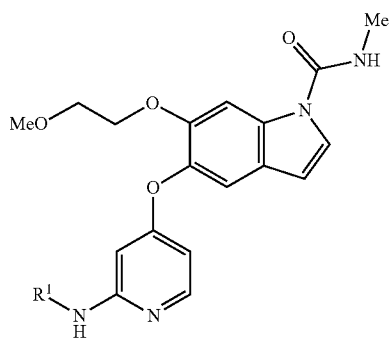

(where $R^1$ represents the same group as specified above), and 2-f) step 2-f) in which $R^1$ of compound (2h) obtained in step 2-e) is removed to produce compound (2i):

(2i)

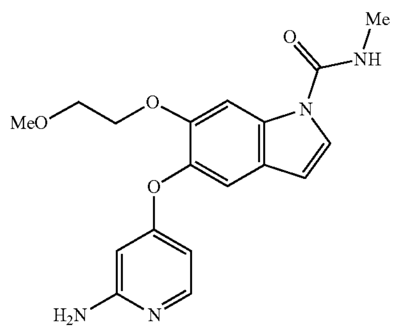

and if necessary step 2-g) in which compound (2i) obtained in step 2-f) is converted to a salt,

[2] The production process according to [1], wherein compound (2b) is 4-nitropyridin-1-ium-oleate,

[3] The production process according to [1], wherein compound (2d) is 1,1,3,3-tetramethylbutylamine,

[4] The production process according to [1], wherein compound (2d) is cumylamine,

[5] The production process according to [1], wherein the activating agent is p-toluenesulfonyl chloride,

[6] A process for producing compound (1g):

(1g)

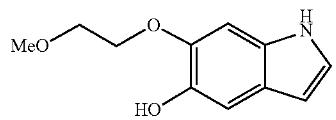

wherein the process comprises:

1-a) step 1-a) in which 1,2-(methylenedioxy)-4-nitrobenzene and 4-bromobenzyl alcohol are reacted in the presence of a base to produce compound (1c):

(1c)

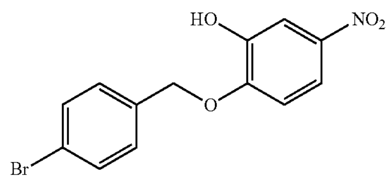 [SMILES: O=[N+]([O-])c1ccc(OCc2ccc(Br)cc2)c(O)c1]

1-b) step 1-b) in which compound (1c) obtained in step 1-a) and a methoxyethylating agent are reacted in the presence of a base to produce compound (1d):

(1d)

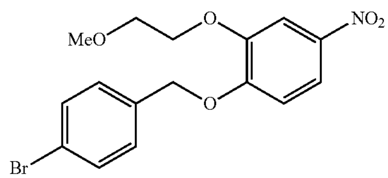 [SMILES: COCCOc1cc([N+](=O)[O-])ccc1OCc1ccc(Br)cc1]

1-c) step 1-c) in which compound (1d) obtained in step 1-b) and a cyanomethylating agent are reacted in the presence of a base to produce compound (1f):

(1f)

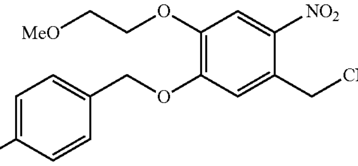

and 1-d) step 1-d) in which compound (1g):

(1g)

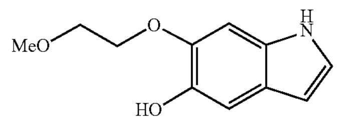

is produced by conversion of the nitro group of compound (1f) obtained in step 1-c) to an amino group, removal of the 4-bromobenzyl group, and ring closure with an acid catalyst, and

[7] The production process according to [6], wherein a palladium catalyst and sulfuric acid are used in step 1-d).

Advantageous Effects of Invention

The present invention can provide a production process allowing high-yield and efficient synthesis of key intermediates for production of E7090.

DESCRIPTION OF EMBODIMENTS

The definitions of the symbols and terms used throughout the present specification will now be explained, prior to a more detailed description of the invention.

The term "$C_{1-6}$ alkyl group" as used herein means a straight-chain or branched substituent of 1 to 6 carbon atoms, which is a monovalent group derived by removing any one hydrogen atom from an aliphatic saturated hydrocarbon of 1 to 6 carbon atoms. Examples of $C_{1-6}$ alkyl groups include methyl, ethyl, 1-propyl, 2-propyl, 2-methyl-1-propyl, 2-methyl-2-propyl, 1-butyl, 2-butyl, 1-pentyl, 2-pentyl, 3-pentyl, 1-hexyl, 2-hexyl and 3-hexyl groups, with methyl and ethyl groups being preferred.

The term "$C_{6-10}$ aryl group" as used herein refers to an aromatic cyclic hydrocarbon group of 6 to 10 carbon atoms. Examples of $C_{6-10}$ aryl groups include phenyl, 1-naphthyl and 2-naphthyl groups, with phenyl being preferred.

The term "halogen atom" as used herein refers to fluorine, chlorine, bromine or iodine, and preferably chlorine or bromine.

The term "base" as used herein may refer to an inorganic base such as lithium hydroxide, sodium hydroxide, potassium hydroxide, lithium carbonate, sodium carbonate, potassium carbonate, potassium tert-butoxide, sodium tert-butoxide, sodium hydrogencarbonate, potassium hydrogencarbonate or cesium carbonate: an organometallic reagent such as butyllithium, methyllithium, lithium bis(trimethylsilyl)amide, sodium bis(trimethylsilyl)amide or potassium bis(trimethylsilyl)amide; a hydride such as lithium hydride, sodium hydride or potassium hydride: a heterocyclic compound such as imidazole, pyridine, dimethylpyridine, trimethylpyridine or 4-dimethylaminopyridine; or an organic amine such as triethylamine, N,N-diisopropylethylamine or diazabicycloundecene.

The term "compound" as used herein includes anhydrides, hydrates and solvates.

The term "salt" as used herein refers to, for example, inorganic acid salts (such as sulfates, nitrates, perchlorates, phosphates, carbonates, bicarbonates, hydrofluorides, hydrochlorides, hydrobromides and hydroiodides), organic carboxylic acid salts (such as acetates, oxalates, maleates, fumarates, succinates, tartrates and citrates), organic sulfonic acid salts (such as methanesulfonates, trifluoromethanesulfonates, ethanesulfonates, benzenesulfonates, toluenesulfonates and camphorsulfonates), and salts of acidic amino acids (such as aspartates and glutamates).

There are no particular restrictions on salts of compound (2i), and examples include inorganic acid salts, organic acid salts and acidic amino acid salts.

The production process of the invention will now be explained in greater detail.

Production Process 1 Process for Producing Compound (1g)

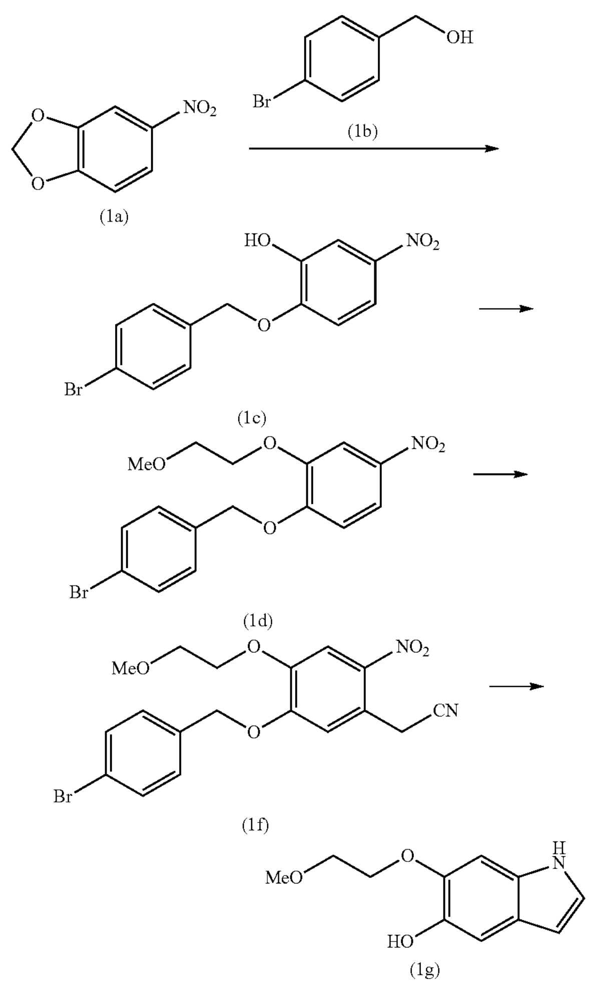

Step 1-a) is a step in which 1,2-(methylenedioxy)-4-nitrobenzene (compound (1a)) and 4-bromobenzyl alcohol (compound (1b)) are reacted in the presence of a base to obtain compound (1c).

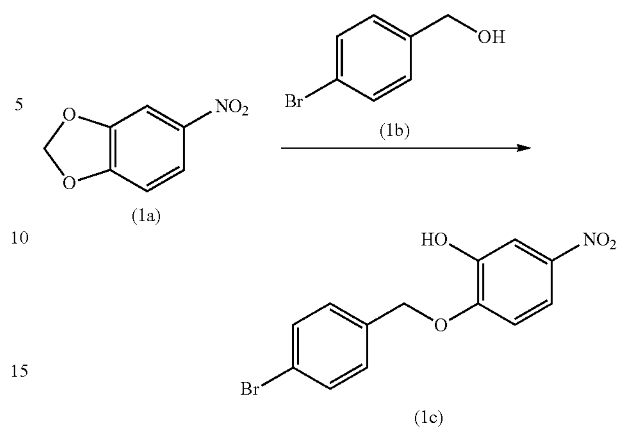

The 4-bromobenzyl alcohol may be used at 1.0 to 2.0 equivalents with respect to compound (1a). It is preferably used at 1.1 to 1.3 equivalents.

The base used may be potassium hydroxide, sodium hydroxide, potassium carbonate, sodium carbonate, cesium carbonate, potassium tert-butoxide, sodium tert-butoxide or sodium hydride. It is preferably sodium tert-butoxide. The base may be used at 1.0 to 5.0 equivalents with respect to compound (1a). It is preferably used at 1.0 to 3.0 equivalents.

The solvent is not particularly restricted so long as it dissolves the starting substance and does not interfere with the reaction, and for example, it may be N,N-dimethylformamide, dimethyl sulfoxide, N,N-dimethylacetamide, 1,3-dimethyl-2-imidazolidinone, tetrahydrofuran, or a mixed solvent thereof. It is preferably a mixed solvent of dimethyl sulfoxide and tetrahydrofuran.

The reaction temperature will generally differ depending on the starting substances, solvent and other reagents used in the reaction, but it is preferably 0° C. to 30° C. The temperature is preferably 5° C. to 20° C.

Step 1-b) is a step in which compound (1c) and a methoxyethylating agent are reacted in the presence of a base to obtain compound (1d).

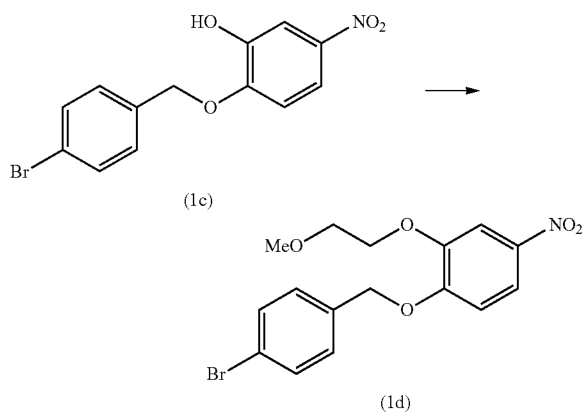

Examples of methoxyethylating agents include 2-chloroethyl methyl ether, 2-bromoethyl methyl ether and 2-iodoethyl methyl ether. A preferred one is 2-bromoethyl methyl ether. The methoxyethylating agent may be used at 1.0 to 2.0 equivalents with respect to compound (1c). It is preferably used at 1.0 to 1.2 equivalents.

The base used may be potassium hydroxide, sodium hydroxide, potassium carbonate, sodium carbonate, cesium carbonate, potassium tert-butoxide, sodium tert-butoxide or sodium hydride. It is preferably potassium carbonate. The base may be used at 1.0 to 5.0 equivalents with respect to compound (1d). It is preferably used at 1.1 to 1.3 equivalents.

The solvent is not particularly restricted so long as it dissolves the starting substance and does not interfere with the reaction, and for example, it may be N,N-dimethylformamide, dimethyl sulfoxide, N,N-dimethylacetamide or 1,3-dimethyl-2-imidazolidinone. It is preferably N,N-dimethylformamide.

The reaction temperature will generally differ depending on the starting substances, solvent and other reagents used in the reaction, but it is preferably room temperature to 80° C. The temperature is preferably 40° C. to 70° C.

Step 1-c) is a step in which compound (1d) and a cyanomethylating agent are reacted in the presence of a base to obtain compound (1f).

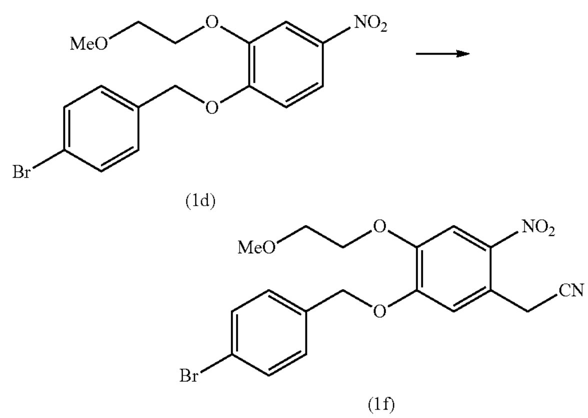

(1d)

(1f)

Examples of cyanomethylating agents include 4-chlorophenoxyacetonitrile, 4-bromophenoxyacetonitrile, phenoxyacetonitrile, 2-chloroacetonitrile, 2-bromoacetonitrile, 2-iodoacetonitrile and (cyanomethyl)trimethylammonium iodide. A preferred one is 4-chlorophenoxyacetonitrile. The cyanomethylating agent may be used at 1.0 to 2.0 equivalents with respect to compound (1d). It is preferably used at 1.2 to 1.4 equivalents.

The base used may be potassium hydroxide, sodium hydroxide, potassium carbonate, sodium carbonate, cesium carbonate, potassium tert-butoxide, sodium tert-butoxide or sodium hydride. It is preferably potassium tert-butoxide. The base may be used at 1.0 to 5.0 equivalents with respect to compound (1d). It is preferably used at 2.0 to 4.0 equivalents.

The solvent is not particularly restricted so long as it dissolves the starting substance and does not interfere with the reaction, and for example, it may be N,N-dimethylformamide, dimethyl sulfoxide, N,N-dimethylacetamide or 1,3-dimethyl-2-imidazolidinone. It is preferably N,N-dimethylformamide.

The reaction temperature will generally differ depending on the starting substances, solvent and other reagents used in the reaction, but it is preferably −70° C. to room temperature. The temperature is preferably −70° C. to −50° C.

Step 1-d) is a step in which compound (1g) is obtained by conversion of the nitro group in compound (1f) to an amino group, removal of the 4-bromobenzyl group, and ring closure with an acid catalyst.

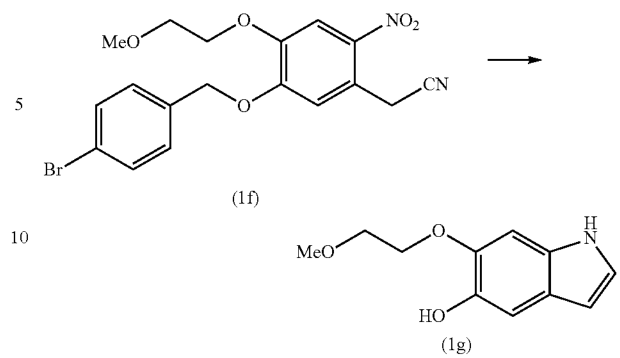

(1f)

(1g)

A reduction catalyst may be used in a hydrogen atmosphere for conversion of the nitro group to an amino group and removal of the 4-bromobenzyl group. Examples of reduction catalysts include palladium carbon, palladium black and platinum oxide. It is preferred to use palladium carbon under a hydrogen atmosphere.

The reaction solvent is not particularly restricted so long as it dissolves the starting substance and does not interfere with the reaction, and for example, it may be tetrahydrofuran, methanol, ethanol, water, or a mixture thereof such as tetrahydrofuran and water, tetrahydrofuran and methanol or tetrahydrofuran and ethanol. It is preferably a mixed solvent of tetrahydrofuran and water.

The acid catalyst may be hydrochloric acid, sulfuric acid or acetic acid. It is preferably sulfuric acid. The concentration of the acid catalyst that is used may be 0.01 N to 1.0 N. The concentration is preferably 0.01 N to 0.2 N. The reaction temperature will generally differ depending on the starting substances, solvent and other reagents used in the reaction, but it is preferably room temperature to 60° C. The temperature is preferably 30° C. to 50° C.

Production Process 2 Process for Producing Compound (2i)

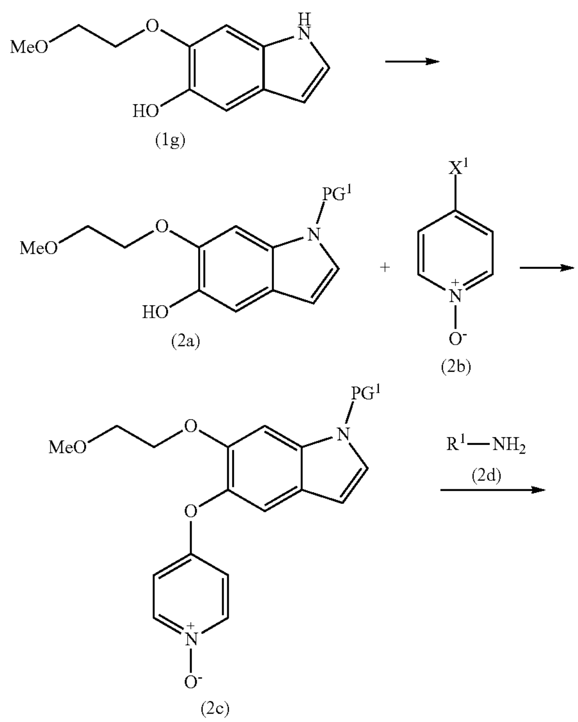

(1g)

(2a)

(2b)

(2c)

-continued

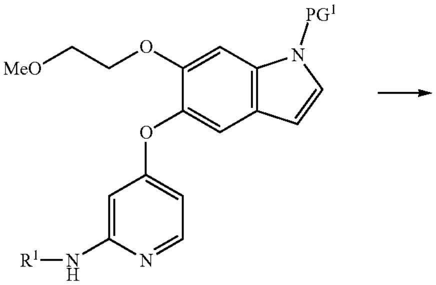

(2e)

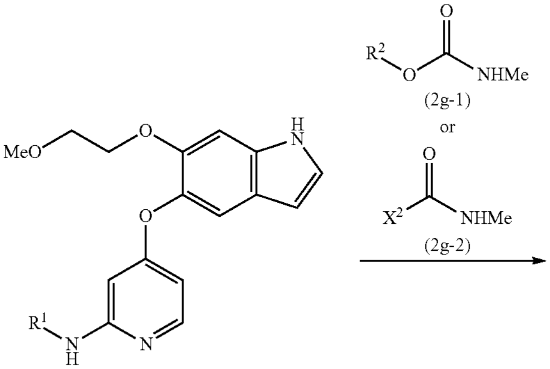

(2f)

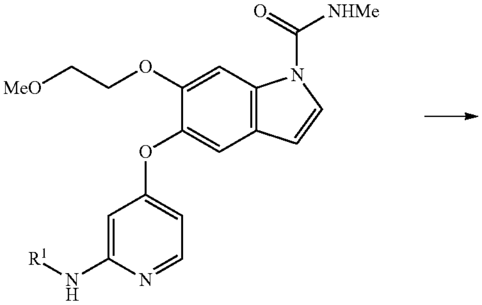

(2h)

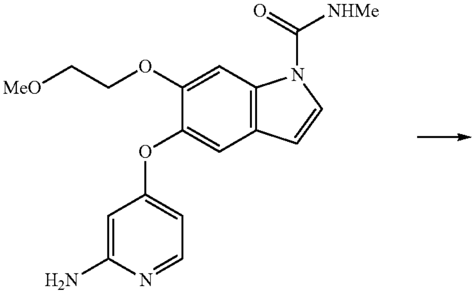

(2i)

-continued

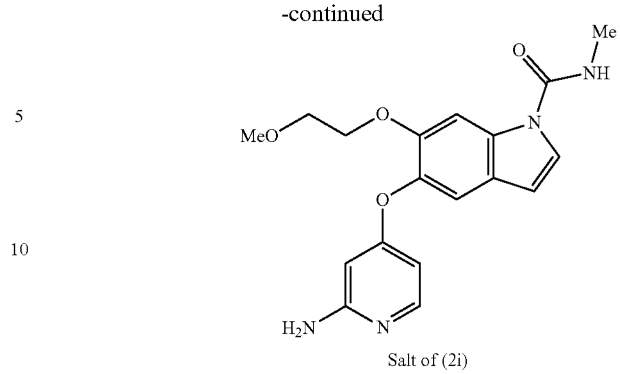

Salt of (2i)

Step 2-a) is a step of introducing a protecting group into compound (1g) to obtain compound (2a).

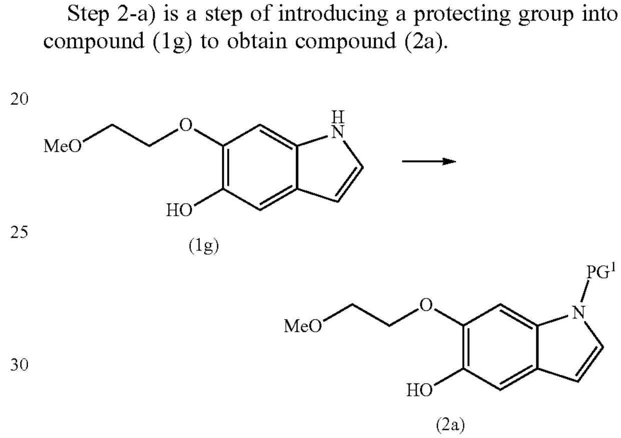

(2a)

The protecting group introduced may be a tert-butoxycarbonyl, benzyloxycarbonyl, benzoyl, acetyl or trifluoroacetyl group. It is preferably a tert-butoxycarbonyl group. A di-tert-butyl-dicarbonate or tert-butoxycarbonyl chloride compound may be used to introduce the tert-butoxycarbonyl group. Such a compound is preferably di-tert-butyl-dicarbonate. The di-tert-butyl-dicarbonate may be used at 1 to 5 equivalents with respect to compound (1g). It is preferably used at 2.0 to 2.5 equivalents.

When di-tert-butyl-dicarbonate is used, the base used is preferably triethylamine, N-methylimidazole or N,N-dimethylaminopyridine (DMAP). Preferably, N,N-dimethylaminopyridine (DMAP) is used. When di-tert-butyl-dicarbonate is used, the N,N-dimethylaminopyridine (DMAP) may be used at 0.01 to 2.0 equivalents with respect to compound (1g). It is preferably used at 0.05 to 0.2 equivalents.

The solvent is not particularly restricted so long as it dissolves the starting substance and does not interfere with the reaction, and for example, it may be tetrahydrofuran, N,N-dimethylformamide, acetonitrile or ethyl acetate. The solvent is preferably tetrahydrofuran.

The reaction temperature will generally differ depending on the starting substances, solvent and other reagents used in the reaction, but it is preferably 0° C. to 60° C. The temperature is preferably 20° C. to 30° C.

In step 2-a), the hydroxyl groups may be selectively deprotected, under suitable conditions depending on the protecting group. For example, deprotection can be easily carried out under hydrolysis conditions for tert-butoxycarbonyl or benzyloxycarbonyl groups. For hydrolysis of a di-tert-butoxycarbonyl compound, in particular, the base used may be sodium hydroxide, potassium hydroxide, sodium carbonate or potassium carbonate, for example. The base is preferably potassium carbonate. The potassium carbonate may be used at 0.7 to 1.2 equivalents with respect to compound (1g). It is preferably used at 0.7 to 0.9 equivalents.

The solvent is not particularly restricted so long as it dissolves the starting substance and does not interfere with the reaction, and for example, it may be methanol, ethanol, isopropyl alcohol, acetonitrile, water, or a mixture of these solvents. The solvent is preferably methanol.

The reaction temperature will generally differ depending on the starting substances, solvent and other reagents used in the reaction, but it is preferably 25° C. to 50° C. The temperature is preferably 30° C. to 40° C.

Step 2-b) is a step in which compound (2a) and compound (2b) are reacted in the presence of a base to obtain compound (2c).

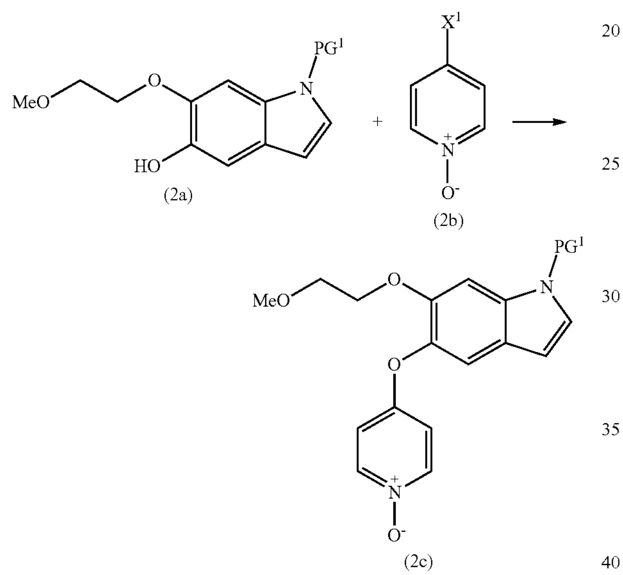

(2a) (2b) (2c)

Compound (2b) may be 4-chloropyridin-1-ium-oleate, 4-bromopyridin-1-ium-oleate or 4-nitropyridin-1-ium-oleate. It is preferably 4-nitropyridin-1-ium-oleate. Compound (2b) may be used at 1.0 to 1.4 equivalents with respect to compound (2a). It is preferably used at 1.1 to 1.3 equivalents.

The base used may be potassium carbonate, cesium carbonate or potassium tert-butoxide, or a 48% potassium hydroxide aqueous solution. It is preferably cesium carbonate. The base may be used at 1 to 3 equivalents with respect to compound (2a). It is preferably used at 1.4 to 1.6 equivalents.

The solvent is not particularly restricted so long as it dissolves the starting substance and does not interfere with the reaction, and for example, it may be N,N-dimethylformamide, N,N-dimethylacetamide, or dimethyl sulfoxide 1,3-dimethyl-2-imidazolidinone. It is preferably dimethyl sulfoxide.

The reaction temperature will generally differ depending on the starting substances, solvent and other reagents used in the reaction, but it is preferably 0° C. to 60° C. The temperature is preferably 30° C. to 50° C.

Step 2-c) is a step in which compound (2c) and compound (2d) are reacted in the presence of an activating agent to obtain compound (2e).

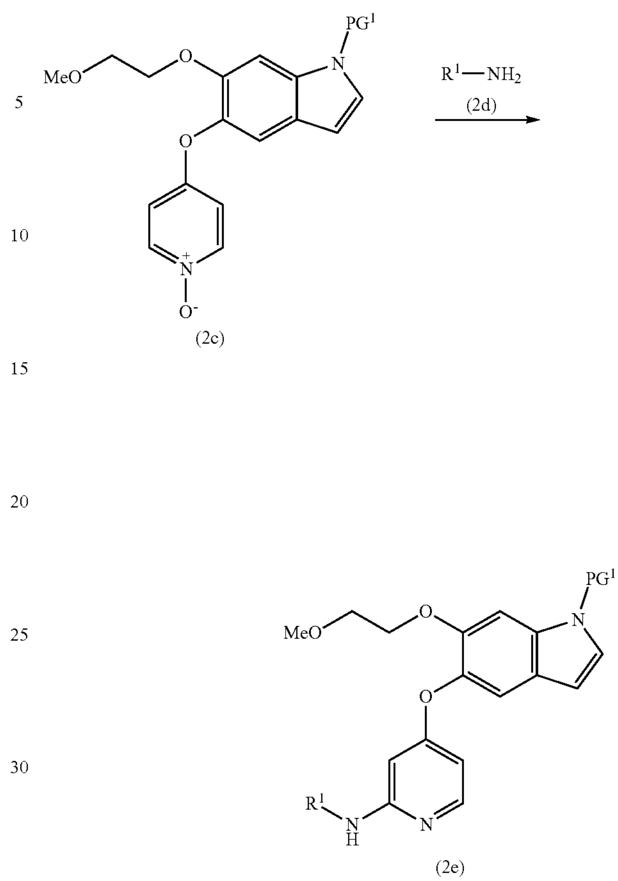

(2c) (2e)

Examples for compound (2d) include tert-butylamine, tert-pentylamine, cumylamine and tert-octylamine. It is preferably tert-octylamine. Compound (2d) may be used at 1 to 15 equivalents with respect to compound (2c). It is preferably used at 5 to 10 equivalents.

The activating agent may be p-toluenesulfonyl chloride, benzenesulfonyl chloride, p-chlorosulfonyl chloride, p-methoxysulfonyl chloride, 2-methylsulfonyl chloride, 1-naphthylsulfonyl chloride, 2,4,6-trimethylsulfonyl chloride or 2,4,6-triphenylsulfonyl chloride. It is preferably p-toluenesulfonyl chloride. The equivalent amount of the activating agent may be 1 to 5 equivalents with respect to compound (2c). It is preferably used at 1.5 to 2.5 equivalents.

The solvent is not particularly restricted so long as it dissolves the starting substance and does not interfere with the reaction, and for example, it may be trifluoromethylbenzene, toluene, ethyl acetate, isopropyl acetate, tetrahydrofuran, 2-methyltetrahydrofuran, tert-butyl methyl ether, dimethoxyethane, cyclopentyl methyl ether, 4-methyltetrahydropyran, water, or a mixture of the foregoing. It is preferably a mixed solvent of toluene, 4-methyltetrahydropyran and water.

The reaction temperature will generally differ depending on the starting substances, solvent and other reagents used in the reaction, but it is preferably −50° C. to room temperature, and preferably −20° C. to 10° C.

Step 2-d) is a step in which $PG^1$ is removed from compound (2e) to obtain compound (2f).

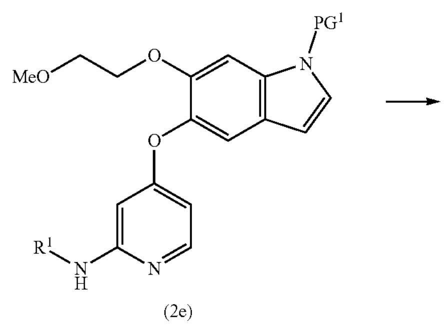

(2e)

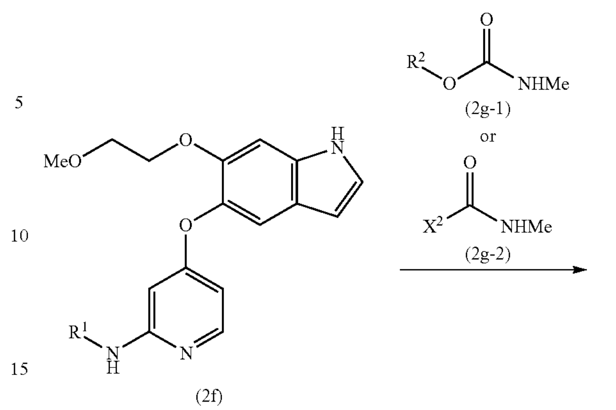

(2f)

(2g-1)

or (2g-2)

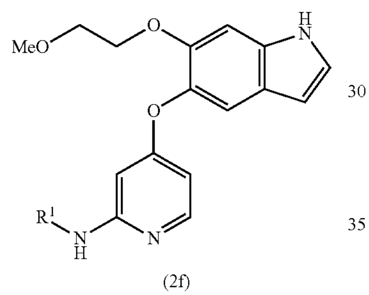

(2f)

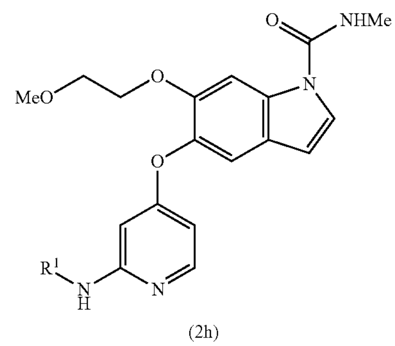

(2h)

In step 2-d), deprotection may be carried out under deprotection conditions suited for the protecting group. In the case of a tert-butoxycarbonyl or benzyloxycarbonyl group, for example, deprotection may be carried out under basic conditions. The base used may be sodium hydroxide, potassium hydroxide, sodium tert-butoxide, potassium tert-butoxide, potassium carbonate, tert-butylamine, sodium methoxide or sodium ethoxide, for example. It is preferably sodium hydroxide. The base is used at preferably 1 to 10 equivalents and more preferably 2 to 4 equivalents with respect to compound (2e).

The solvent is not particularly restricted so long as it dissolves the starting substance and does not interfere with the reaction, and for example, it may be ethanol, tetrahydrofuran, dimethyl sulfoxide, methanol, water, or a mixture of these solvents. In the case of a tert-butoxycarbonyl group, for example, the solvent is preferably a mixture of ethanol, tetrahydrofuran and water. The reaction temperature will generally differ depending on the starting substances, solvent and other reagents used in the reaction, but it is preferably 30° C. to 70° C. The temperature is preferably 40° C. to 60° C.

Step 2-e) is a step in which compound (2f) and compound (2g-1) or compound (2g-2) are reacted in the presence of a base to obtain compound (2h).

Compound (2g-1) or compound (2g-2) may be phenylmethyl carbamate, ethylmethyl carbamate, methylaminocarbonyl chloride or methylaminocarbonyl bromide, for example. A preferred compound is phenylmethyl carbamate. Phenylmethyl carbamate, for example, may be used at 1.0 to 2.0 equivalents with respect to compound (2f). It is preferably used at 1.2 to 1.4 equivalents.

The base used may be sodium hydroxide, potassium hydroxide, sodium tert-butoxide or potassium tert-butoxide. It is preferably potassium tert-butoxide. The base may be used at 0.1 to 3.0 equivalents with respect to compound (2f). It is preferably used at 1.0 to 1.5 equivalents.

The solvent is not particularly restricted so long as it dissolves the starting substance and does not interfere with the reaction, and for example, it may be tetrahydrofuran, dimethylformamide or dimethyl sulfoxide, or a mixture of these solvents. It is preferably a mixed solvent of tetrahydrofuran and dimethyl sulfoxide.

The reaction temperature will generally differ depending on the starting substances, solvent and other reagents used in the reaction, but it is preferably −10° C. to room temperature. The temperature is more preferably 0° C.

Step 2-f) is a step in which $R^1$ is removed from compound (2h) to obtain compound (2i), and then if necessary a salt of compound (2i) is obtained.

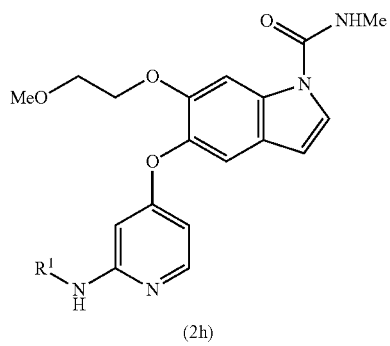

(2h)

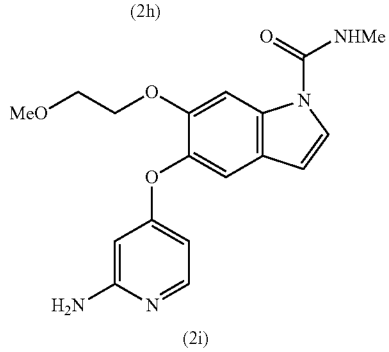

(2i)

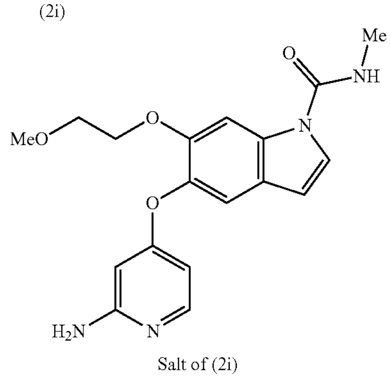

Salt of (2i)

The conditions for removal of $R^1$ in step 2-f) may be selected depending on the type of $R^1$ group. When $R^1$ is a cumyl or octyl group, for example, the acid used may be hydrochloric acid, sulfuric acid, formic acid or methanesulfonic acid. It is preferably methanesulfonic acid.

Compound (2i) can be converted to a salt by acid treatment. The salt may be, for example, inorganic acid salts (such as sulfates, nitrates, perchlorates, phosphates, carbonates, bicarbonates, hydrofluorides, hydrochlorides, hydrobromides and hydroiodides), organic carboxylic acid salts (such as acetates, oxalates, maleates, tartrates, fumarates and citrates), organic sulfonic acid salts (such as methanesulfonates, trifluoromethanesulfonates, ethanesulfonates, benzenesulfonates, toluenesulfonates and camphorsulfonates), and salts of amino acids (such as aspartates and glutamates). The salt is preferably a methanesulfonate. Compound (2i) can be stably stored for long periods if it is converted to a salt. A process for synthesizing a methanesulfonate of compound (2i) by removal of $R^1$ from compound (2h) will now be explained as an example.

Methanesulfonic acid may be used at 1 to 20 equivalents with respect to compound (2h). It is preferably used at 5 to 10 equivalents.

The reaction solvent is not particularly restricted so long as it dissolves the starting substance and does not interfere with the reaction, and for example, it may be ethanol, methanol or dimethoxyethane, or a mixture of these solvents. It is preferably a mixed solvent of ethanol and methanol. The reaction temperature will generally differ depending on the starting substances, solvent and other reagents used in the reaction, but it is preferably room temperature to 80° C. The temperature is preferably 20° C. to 50° C.

EXAMPLES

The present invention will now be explained in greater detail by Examples. However, the invention is not limited to these Examples. The abbreviations used here throughout are those commonly known to those skilled in the art, and a few are indicated below:

The $^1$H-NMR spectra were measured using a BRUCKER AVANCE NEO 400 (400 MHZ), BRUCKER AVANCE III 500 (500 MHz), BRUCKER AVANCE 600 (600 MHz) or BRUCKER AVANCE NEO 700 (700 MHz).

The chemical shifts in the proton nuclear magnetic resonance ($^1$H-NMR) spectra are recorded in δ units (ppm) with respect to tetramethylsilane, and the coupling constants are recorded in Hertz (Hz). The patterns are indicated as s: singlet, d: doublet, br: broad or m: multiplet.

The term "room temperature" in the Examples generally refers to a temperature between about 10° C. and 35° C. The percentage values are weight percentages, unless otherwise specified.

Example 1: Production of 6-(2-methoxyethoxy)-1H-indole-5-ol (compound (1g))

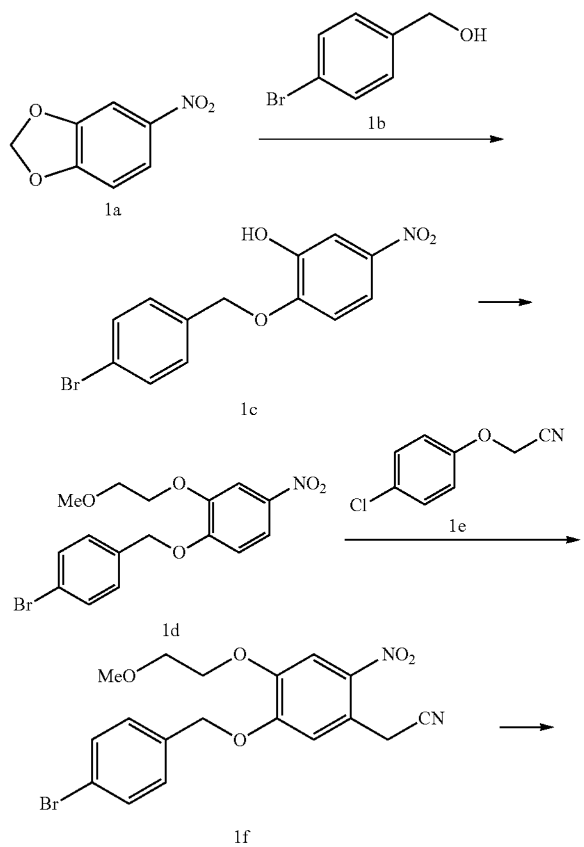

1a 1b 1c 1d 1e 1f

-continued

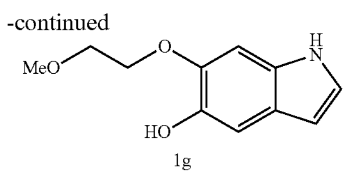

1g

Production Example 1: Production of 2-[(4-bromobenzyl)oxy]-5-nitrophenol (1c)

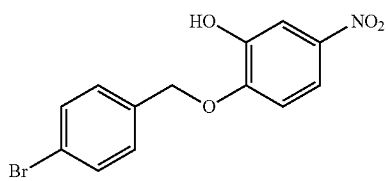

A solution of 4-bromobenzyl alcohol (120.6 kg, 645 mol, 1.2 eq.) and sodium tert-butoxide (103.3 kg, 1075 mol, 2.0 eq.) in dimethyl sulfoxide (450 L) and tetrahydrofuran (157 L) was prepared at 13° C. To this solution was added dropwise a solution of 1,2-(methylenedioxy)-4-nitrobenzene (89.8 kg, 537 mol) in tetrahydrofuran (726 L) and dimethyl sulfoxide (269 L) at 10 to 15° C., and then tetrahydrofuran (14 L) was added and the mixture was stirred at 14° C. for 2 hours. A mixture of water (500 L) and 35% hydrochloric acid (83 L) was added dropwise to the reaction mixture at 30° C. or lower. After then adding isopropyl acetate (450 L), the organic layer was separated off. The organic layer was rinsed with a 7% aqueous sodium bicarbonate solution (290 kg), and then rinsed with 9% brine (296 kg). Isopropyl acetate (900 L) was added to the organic layer, and the mixture was concentrated under reduced pressure to 547 L. Isopropyl acetate (900 L) was added to the concentrated residue, and the mixture was concentrated under reduced pressure to 547 L. Hexane (450 L) was added to the concentrated residue at 26 to 32° C., and after cooling to 10° C. or lower, the precipitated solid was filtered. The crystals were rinsed with an isopropyl acetate (90 L)/methanol (27 L/hexane (180 L) mixture, and the resulting crystals were dried under reduced pressure at an internal temperature of 50° C. or lower to obtain 125 kg of the title compound.

$^1$H NMR Spectrum (DMSO-$d_6$) δ (ppm): 5.23 (2H, s), 7.17 (1H, d, J-9.1 Hz), 7.44 (2H, br d, J=8.3 Hz), 7.60 (2H, br d, J=8.3 Hz), 7.63 (1H, d, J=2.6 Hz), 7.71 (1H, dd, J=9.1, 2.6 Hz)

Production Example 2-1 Production of 1-[(4-bromobenzyl)oxy]-2-(2-methoxyethoxy)-4-nitrobenzene (1d) (1)

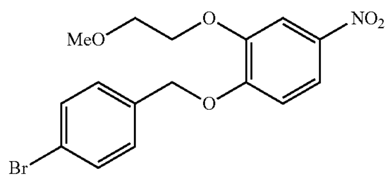 [SMILES: COCCOc1cc([N+](=O)[O-])ccc1OCc1ccc(Br)cc1]

Potassium carbonate (180 g, 1301 mmol, 1.2 eq.) was added to a solution of 2-[(4-bromobenzyl)oxy]-5-nitrophenol (351.4 g, 1084 mmol) in dimethylformamide (1750 mL), and the mixture was stirred. Next, 2-bromoethyl methyl ether (166 g, 1193 mol, 1.1 eq.) was added and the mixture was stirred for 6 days. Ethyl acetate (9000 mL) and water (3000 mL) were added prior to liquid separation of the mixture. After rinsing the organic layer 4 times with water (350 mL), the organic layer was concentrated under reduced pressure at 50° C. Heptane (1500 mL) was added to the concentrated residue to form a suspension, which was filtered to obtain crystals. The filtrate was concentrated under reduced pressure at 50° C., and heptane (1000 mL) was added to the concentrated residue to form a suspension, which was filtered to obtain crystals. The obtained crystals were combined and dried under reduced pressure at 50° C. to obtain 408 g of the title compound.

$^1$H NMR Spectrum (DMSO-$d_6$) δ (ppm): 3.28 (3H, s), 3.68 (2H, t, J=4.5 Hz), 4.23 (2H, t, J-4.2 Hz), 5.26 (2H, s), 7.23 (1H, d, J=9.1 Hz), 7.41 (2H, br d, J=7.9 Hz), 7.60 (2H, br d, J=7.9 Hz), 7.79 (1H, d, J-2.3 Hz), 7.88 (1H, dd, J=8.7, 1.9 Hz)

Production Example 2-2: Production of 1-[(4-bromobenzyl)oxy]-2-(2-methoxyethoxy)-4-nitrobenzene (1d) (2)

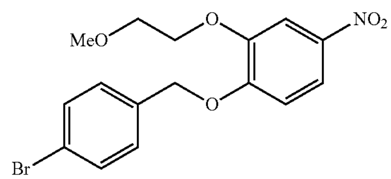

To a solution of 2-bromoethyl methyl ether (29.5 kg, 212 mol, 1.1 eq.) in dimethylformamide (294 kg) were added 2-[(4-bromobenzyl)oxy]-5-nitrophenol (62.5 kg, 193 mol) and potassium carbonate (32.0 kg, 232 mol, 1.2 eq.), and the mixture was stirred at 56 to 60° C. for 6 hours. After cooling, ethyl acetate (1252 L) and water (375 L) were added. After liquid separation, the organic layer was rinsed with water (188 L), and ethyl acetate (83 L) and a 5% aqueous sodium chloride solution (198 kg) were added to the organic layer prior to liquid separation. The organic layer was concentrated under reduced pressure to 737 L, and then a suspension of 1-[(4-bromobenzyl)oxy]-2-(2-methoxyethoxy)-4-nitrobenzene (22.2 g) in methanol (1.7 kg) was added. Methanol (738 L) was added dropwise at 0 to −4° C., and the precipitated crystals were filtered out. The crystals were rinsed with methanol (189 L) and the resulting crystals were dried under reduced pressure at an internal temperature of 50° C. or lower to obtain 66.0 kg of the title compound.

Production Example 3: Production of {5-[(4-bromobenzyl)oxy]-4-(2-methoxyethoxy)-2-nitrophenyl}acetonitrile (1f)

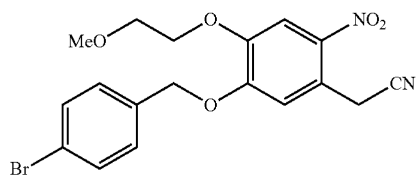 [SMILES: COCCOc1cc([N+](=O)[O-])c(CC#N)cc1OCc1ccc(Br)cc1]

To a solution of potassium tert-butoxide (14.7 kg, 131 mol, 3 eq.) in dimethylformamide (168 L) was added dropwise a solution of 1-[(4-bromobenzyl)oxy]-2-(2-methoxyethoxy)-4-nitrobenzene (16.7 kg, 43.7 mol) and 4-chlorophenoxyacetonitrile (9.5 kg, 56.7 mol, 1.3 eq.) in dimethylformamide (80 L) at −60 to −55° C., and after adding dimethylformamide (21 L), the mixture was stirred at −63 to −58° C. for 2 hours. A mixture of ethyl acetate (351 L) and acetic acid (8 L) was added dropwise to the reaction mixture. After adding a 5% aqueous sodium chloride solution (168 kg), the organic layer was rinsed twice with a 5% aqueous sodium chloride solution (84 kg, 85 kg). Ethyl acetate (34 L) was added to the organic layer, and then rinsed with a 5% aqueous sodium chloride solution (85 kg). The organic layer was concentrated under reduced pressure, and tert-butyl methyl ether (134 L) and methanol (13 L) were added to the concentrated residue, after which the mixture was cooled to 0 to 2° C. and the precipitated solid was filtered out. The obtained crystals were rinsed with a tert-butylmethyl ether (30 L)/ethyl acetate (3 L)/methanol (3 L) mixture, and the resulting crystals were dried under reduced pressure at an internal temperature of 50° C. or lower to obtain 10.7 kg of the title compound. $^1$H-NMR Spectrum ($CDCl_3$) δ (ppm): 3.46 (3H, s), 3.81 (2H, t, J=4.8 Hz), 4.19 (2H, s), 4.25 (2H, t. J=4.4 Hz), 5.23 (2H, s), 7.14 (1H, s), 7.35 (2H, d, J=8.0 Hz), 7.54 (2H, d, J-8.4 Hz), 7.84 (1H, s)

Production Example 4: Production of 6-(2-methoxyethoxy)-1H-indol-5-ol (1g)

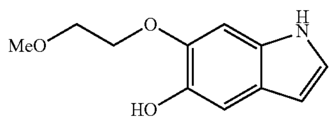 [SMILES: COCCOc1cc2[nH]ccc2cc1O]

To a solution of {5-[(4-bromobenzyl)oxy]-4-(2-methoxyethoxy)-2-nitrophenyl}acetonitrile (28.2 kg, 66.9 mol) in tetrahydrofuran (282 L) were added 10% palladium/carbon (5.7 kg), water (28.2 L) and 98% purified concentrated sulfuric acid (0.21 kg), and the mixture was stirred for 5 hours at 40 to 45° C. and a hydrogen pressure of 0.02 to 0.15 MPa. After the reaction, the catalyst was filtered out, the catalyst residue was rinsed with ethyl acetate (284 L), and the resulting filtrate was separated. A mixture of water (129 L)/hydrochloric acid (12.8 kg) was added dropwise to the organic layer prior to liquid separation. After rinsing the organic layer with 5% sodium bicarbonate solution (141 kg) and 3% brine (146 kg), the organic layer was concentrated under reduced pressure to 85 L. Ethyl acetate (144 L) and a 10% aqueous sodium chloride solution (57 kg) were added to the concentrated residue, and the organic layer was rinsed. The organic layer was concentrated under reduced pressure to 85 L. Heptane (28 L) and sodium sulfate (14.1 kg) were added to the obtained concentrated residue and the mixture was stirred. The liquid mixture was passed through NH silica gel (28.2 kg) that had been wetted with ethyl acetate (141 L), for purification. The NH silica gel was then rinsed off with an ethyl acetate (226 L)heptane (57 L) mixture, and combined with the purified mixture. After concentration under reduced pressure to 85 L at 50° C., heptane (64 L) was added dropwise to the concentrated residue, and the mixture was concentrated under reduced pressure to 85 L at 50° C. Ethyl acetate (27 L) and heptane (60 L) were added and the mixture was cooled to 0 to 10° C., after which the precipitated solid was filtered off. The obtained crystals were rinsed with a heptane (45 L)/ethyl acetate (14 L) mixture. The obtained crystals were dried under reduced pressure at an internal temperature of 50° C. or lower to obtain 7.4 kg of the title compound.

$^1$H NMR Spectrum (DMSO-$d_6$) δ (ppm): 3.32 (3H, s), 3.66-3.69 (2H, m), 4.04-4.07 (2H, m), 6.16 (1H, t, J=2.1 Hz), 6.88 (2H, d, J=4.2 Hz), 7.07 (1H, dd, J=2.8, 2.5 Hz), 8.08 (1H, s), 10.57 (1H, br s)

Production Example 4-2: Recrystallization of 6-(2-methoxyethoxy)-1H-indol-5-ol

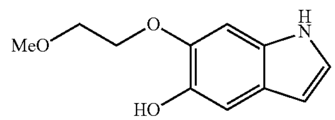 [SMILES: COCCOc1cc2[nH]ccc2cc1O]

A mixture of 6-(2-methoxyethoxy)-1H-indole-5-ol (21.2 kg, 102.3 mol) and ethyl acetate (97 L) was stirred while heating at an internal temperature of 50 to 60° C., and dissolution was confirmed. The solution was clarified by filtration and washed in with ethyl acetate (10 L). It was then cooled to an internal temperature of 40 to 45° C., and after confirming precipitation of crystals, it was stirred for 1 hour at the same temperature. The suspension was cooled to an internal temperature of −10 to 0° C. over a period of 6 hours, and then stirred for 14 hours. After then adding n-heptane (145 kg) dropwise over a period of 1.5 hours, the mixture was stirred for 3 hours at an internal temperature of −10 to 0° C. The suspension was filtered and rinsed with a mixture of ethyl acetate (5.7 kg) and n-heptane (8.7 kg). The obtained crystals were dried under reduced pressure at 40° C. to obtain 20.2 kg of the title compound.

Example 2: Production of 5-((2-aminopyridin-4-yl)oxy)-6-(2-methoxyethoxy)-N-methyl-1H-indole-1-carboxamide methanesulfonate (methanesulfonate of compound (2i)

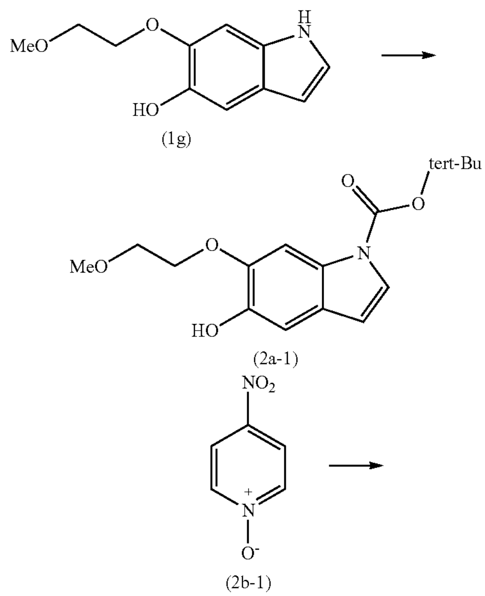

(1g)

(2a-1)

(2b-1)

-continued

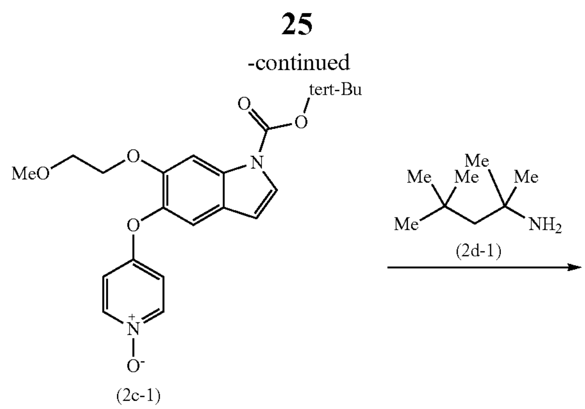

(2d-1)

(2c-1)

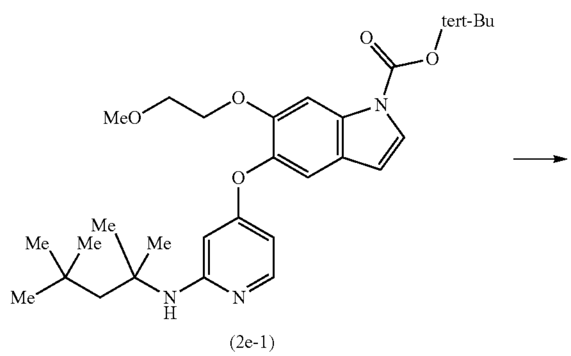

(2e-1)

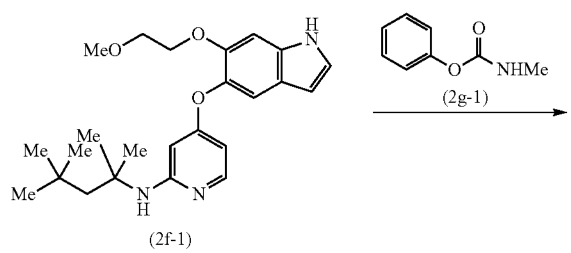

(2g-1)

(2f-1)

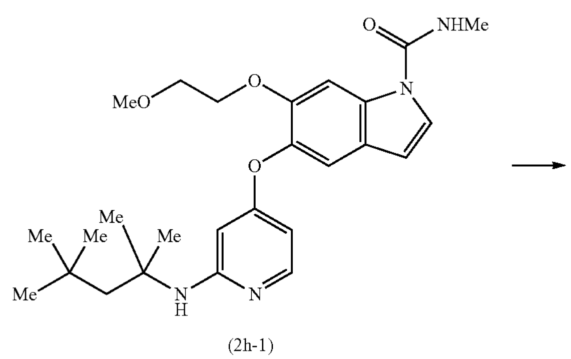

(2h-1)

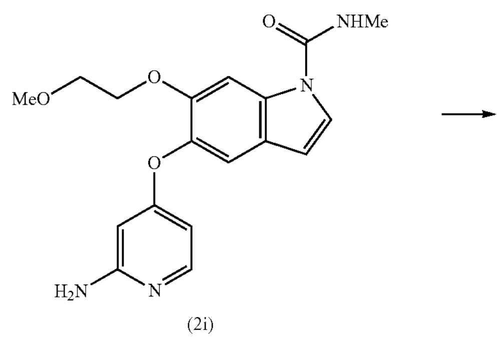

(2i)

-continued

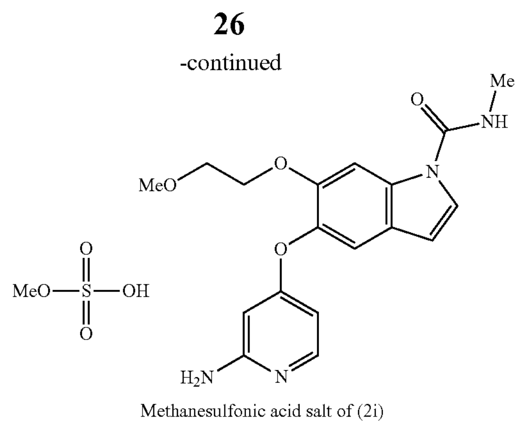

Methanesulfonic acid salt of (2i)

Production Example 5: Production of tert-butyl-5-hydroxy-6-(2-methoxyethoxy)-1H-indole-1-carboxylate (2a-1)

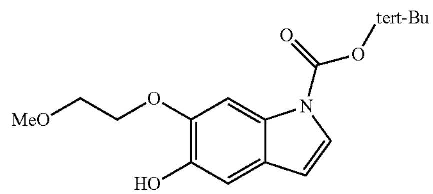

To a suspension of 6-(2-methoxyethoxy)-1H-indole-5-ol (19.8 kg, 95.6 mol) and 4-(dimethylamino)pyridine (1.17 kg, 9.55 mol, 0.1 eq.) in tetrahydrofuran (70.4 kg) was added dropwise a solution of di-tert-butyl-dicarbonate (45.9 kg, 210 mol, 2.2 eq.) in tetrahydrofuran (26.4 kg) under a nitrogen atmosphere, at 25° C. or lower, and it was washed into the mixture with tetrahydrofuran (8.8 kg) and the resulting mixture was stirred for 25° C. for 1 hour. Upon completion of the reaction, the reaction mixture was concentrated under reduced pressure to 90 L, at 40° C. or lower. Methanol (78.3 kg) and potassium carbonate (10.6 kg, 76.4 mol, 0.8 eq.) were added to the obtained concentrate under a nitrogen atmosphere, and the mixture was stirred for 14 hours at 34° C. After cooling the reaction mixture to 25° C., ethyl acetate (178.6 kg) and water (138.6 kg) were added, and 5 N hydrochloric acid (15.2 kg of 35% hydrochloric acid, 16.3 kg water) was added dropwise. After liquid separation, the organic layer was rinsed with 5% brine (3.0 kg salt, 56.4 kg water). The organic layer was concentrated under reduced pressure to 100 L at 50° C. or lower, and then toluene (85.6 kg) was used twice for azeotropic distillation. Dimethyl sulfoxide (87.1 kg) was added to the obtained concentrate and the mixture was concentrated under reduced pressure to 100 L, to obtain a crude product of the title compound (29.4 kg content as 100%) as a dimethyl sulfoxide solution (100 L).

$^1$H NMR Spectrum (DMSO-$d_6$) δ (ppm): 1.61 (9H, s), 3.32 (3H, s), 3.68-3.71 (2H, m), 4.08-4.11 (2H, m), 6.49 (1H, d, J=3.6 Hz), 6.95 (1H, s), 7.44 (1H, d, J=3.6 Hz), 7.59 (1H, s), 8.75 (1H, s)

Production Example 6: Production of tert-butyl-6-(2-methoxyethoxy)-5-[(1-oxo-1λ$^5$-pyridin-4-yl)oxy]-1H-indole-1-carboxylate (2c-1)

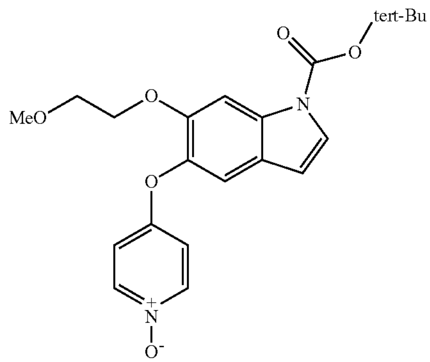

To a solution of tert-butyl-5-hydroxy-6-(2-methoxyethoxy)-1H-indole-1-carboxylate in dimethyl sulfoxide (100 L) (content: 29.4 kg, 95.6 mol) were added 4-nitropyridin-1-ium-oleate (16.1 kg, 115 mol, 1.2 eq.) and dimethyl sulfoxide (106.5 kg). Cesium carbonate (46.7 kg, 143 mol, 1.5 eq.) was added in 7 portions every 30 minutes at 40° C. under a nitrogen atmosphere, and the mixture was then stirred for 3 hours. Upon completion of the reaction, the reaction mixture was cooled to 15° C. or lower, 2-methyltetrahydrofuran (252.5 kg) was added, and water (293.6 kg) was added dropwise prior to liquid separation. The aqueous layer was extracted with 2-methyltetrahydrofuran (126.3 kg), and the combined organic layer was rinsed with 10% brine (8.8 kg salt, 79.2 kg water). The obtained organic layer was concentrated under reduced pressure to 130 L at 50° C. or lower, and further subjected to azeotropic distillation 3 times with toluene (127.0 kg). Toluene (48.4 kg) was added to the concentrate, the mixture was heated to 55° C., and the resulting suspension was cooled to −15° C., after which it was filtered and rinsed with toluene (51.0 kg). The obtained crystals were dried under reduced pressure at 50° C. or lower to obtain 28.61 kg of the title compound.

$^1$H NMR Spectrum (DMSO-d$_6$) δ (ppm): 1.63 (9H, s), 3.16 (3H, s), 3.49-3.52 (2H, m), 4.09-4.12 (2H, m), 6.65 (1H, d, J=3.8 Hz), 6.83-6.87 (2H, m), 7.48 (1H, s), 7.62 (1H, d, J=3.6 Hz), 7.82 (1H, br s), 8.04-8.07 (2H, m)

Production Example 7: Production of 6-(2-methoxyethoxy)-N-methyl-5-({2-[(2,4,4-trimethylpentan-2-yl)amino]pyridin-4-yl}oxy)-1H-indole-1-carboxamide (2e-1)

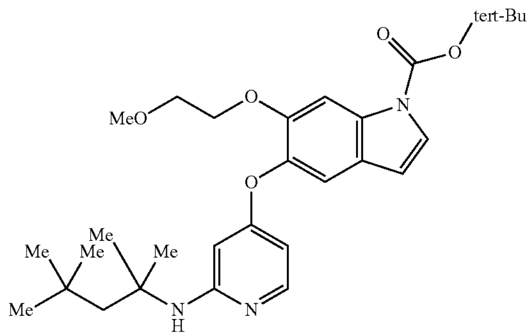

After adding 1,1,3,3-tetramethylbutylamine (64.4 kg, 498 mol, 7.0 eq.) and water (0.4 kg, 0.3 eq.) to a suspension of tert-butyl-6-(2-methoxyethoxy)-5-[(1-oxo-1λ-pyridin-4-yl)oxy]-1H-indole-1-carboxy late (28.5 kg, 71.2 mol) in toluene (431.4 kg), it was washed into the mixture with toluene (12.3 kg) and the mixture was stirred at −5° C. or lower. A mixed solution of p-toluenesulfonyl chloride (28.5 kg, 149 mol, 2.1 eq.) in 4-methyltetrahydropyran (6.1 kg) and toluene (98.6 kg) was added dropwise under a nitrogen atmosphere, and it was washed into the mixture with toluene (24.7 kg) and then it was stirred for 4 hours at −10° C. Upon completion of the reaction, water (159.6 kg) was added dropwise to the reaction mixture prior to liquid separation. After addition of 5 N hydrochloric acid (20.8 kg of 35% hydrochloric acid, 22.3 kg water) to the organic layer and liquid separation, the organic layer was rinsed with water (142.5 kg). After subsequent addition of an aqueous 0.5 N sodium hydroxide solution (2.8 kg caustic soda flake, 142.2 kg water) to the organic layer, and liquid separation, the organic layer was rinsed with water (142.5 kg). The obtained organic layer was concentrated under reduced pressure to 80 L at 50° C. or lower, ethanol (67.5 kg) was added, and the mixture was concentrated under reduced pressure to 80 L. Ethanol (67.3 kg) was added to the concentrate and the mixture was stirred at 0° C. for 2 hours. The precipitate was removed by filtration and washed in with ethanol (67.8 kg), and the filtrate was concentrated under reduced pressure to 80 L. Ethanol (112.4 kg) was added to the obtained concentrate and the mixture was concentrated under reduced pressure to 80 L, to obtain a crude product of the title compound (33.5 kg content as 92%) as an ethanol solution (80 L).

Production Example 8: Production of 4-{[6-(2-methoxyethoxy)-1H-indol-5-yl]oxy}-N-(2,4,4-trimethylpentan-2-yl)pyridine-2-amine (2f-1)

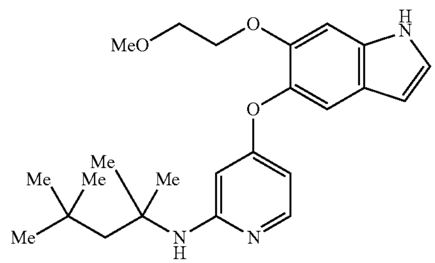 [SMILES: COCCOc1cc2[nH]ccc2cc1Oc1ccnc(NC(C)(C)CC(C)(C)C)c1]

To a solution of 6-(2-methoxyethoxy)-N-methyl-5-({2-[(2,4,4-trimethylpentan-2-yl)amino]pyridin-4-yl}oxy)-1H-indole-1-carboxamide (33.5 kg content, 65.5 mol) in ethanol (80 L) were added ethanol (26.9 kg) and tetrahydrofuran (89.3 kg). An aqueous 5 N sodium hydroxide solution (7.9 kg caustic soda flake, 197 mol, 3.0 eq., 38.2 kg water) was added under a nitrogen atmosphere, and the mixture was stirred at 48° C. for 5 hours. Upon completion of the reaction, the reaction mixture was cooled to 20° C., and methyl tert-butyl ether (173.8 kg), water (115.1 kg) and 5 N hydrochloric acid (15.0 kg of 35% hydrochloric acid, 15.9 kg water) were added prior to liquid separation. Tetrahydrofuran (59.5 kg) and 5% brine (16.8 kg salt, 150.6 kg water) were added to the organic layer prior to liquid separation. The obtained organic layer was concentrated under reduced pressure to 170 L at 50° C. or lower, n-propanol (188.1 kg) was added, and the mixture was concentrated under reduced pressure to 160 L. Methyl tert-butyl ether (49.7 kg) was added to the concentrate and the mixture was stirred for at 48° C. 73 minutes. The suspension was cooled to 0° C. and then filtered and rinsed with n-propanol (53.6 kg). The obtained crystals were dried under reduced pressure at 50° C. or lower to obtain 22.93 kg of the title compound.

$^1$H NMR Spectrum ($CD_3OD$) δ (ppm): 0.89 (9H, s), 1.30 (6H, s), 1.64 (2H, s), 3.27 (3H, s), 3.56-3.59 (2H, m), 4.05-4.09 (2H, m), 5.85 (1H, d, J=2.3 Hz), 6.15 (1H, dd, J=6.0, 2.3 Hz), 6.36-6.39 (1H, m), 7.11 (1H, s), 7.17 (1H, d, J=3.4 Hz), 7.25 (1H, s), 7.74 (1H, d, J=6.0 Hz)

Production Example 9: Production of 6-(2-methoxyethoxy)-N-methyl-5-({2-[(2,4,4-trimethylpentan-2-yl)amino]pyridin-4-yl}oxy)-1H-indole-1-carboxamide (2h-1)

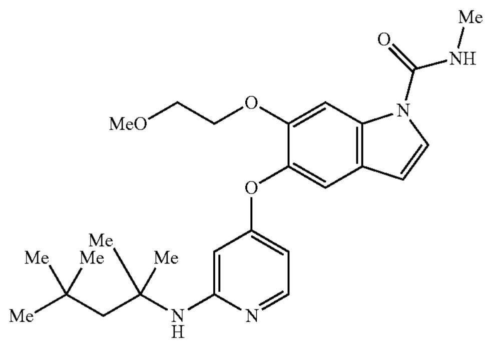 [SMILES: CNC(=O)n1ccc2cc(Oc3ccnc(NC(C)(C)CC(C)(C)C)c3)c(OCCOC)cc21]

Tetrahydrofuran (109.3 kg) was added to 4-{[6-(2-methoxyethoxy)-1H-indol-5-yl]oxy}-N-(2,4,4-trimethylpentan-2-yl)pyridine-2-ami ne (20.5 kg, 49.8 mol), and the mixture was stirred at 5° C. or lower. A solution of potassium tert-butoxide (5.9 kg, 52 mol, 1.05 eq.) in DMSO (22.6 kg) was added dropwise under a nitrogen atmosphere, and the mixture was washed in with DMSO (2.3 kg) and stirred at 0° C. for 30 minutes. A solution of phenylmethyl carbamate (9.0 kg, 60 mol, 1.30 eq.) in tetrahydrofuran (18.2 kg) was added dropwise, and the mixture was washed in with tetrahydrofuran (9.1 kg) and stirred at 0° C. for 5 minutes. Upon completion of the reaction, water (143.5 kg) and isopropyl acetate (125.1 kg) were added to the reaction mixture which was then stirred at 20° C. prior to liquid separation. After addition of an aqueous 1 N sodium hydroxide solution (4.1 kg caustic soda flake, 102.5 kg water) to the organic layer and liquid separation, a 10% aqueous ammonium chloride solution (10.3 kg ammonium chloride, 92.3 kg water) was added prior to liquid separation. The organic layer was rinsed with 1% brine (1.0 kg salt, 102.5 kg water), after which the rinsed organic layer was concentrated under reduced pressure to 80 L at 40° C. or lower, and subjected to azeotropic distillation 3 times with ethanol (80.9 kg), to obtain a crude product of the title compound (23.34 kg content as 100%) as an ethanol solution (80 L).

$^1$H NMR Spectrum ($CD_3OD$) δ (ppm): 0.93 (9H, s), 1.35 (6H, s), 1.71 (2H, s), 2.98 (3H, s), 3.30 (3H, s), 3.62-3.64 (2H, m), 4.13-4.16 (2H, m), 5.88 (1H, d, J=2.3 Hz), 6.18 (1H, dd, J=5.9, 2.3 Hz), 6.61 (1H, d, J=3.2 Hz), 7.32 (1H, s), 7.58 (1H, d, J=3.8 Hz), 7.79 (1H, d, J=5.9 Hz), 8.08 (1H, s)

Production Example 10: Production of 5-((2-aminopyridin-4-yl)oxy)-6-(2-methoxyethoxy)-N-methyl-1H-indole-1-carboxamide methanesulfonate (methanesulfonate of (2i))

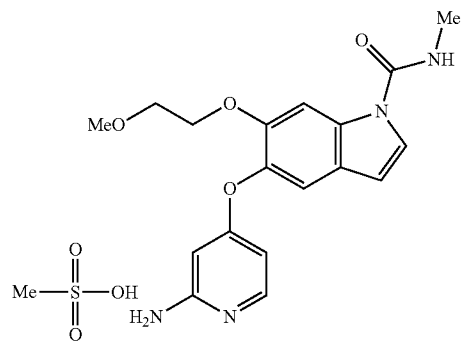

A solution of 6-(2-methoxyethoxy)-N-methyl-5-({2-[(2,4,4-trimethylpentan-2-yl)amino]pyridin-4-yl}oxy)-1H-indole-1-carboxamide (content: 26.0 kg, 55.5 mol) in ethanol (90 L) was concentrated under reduced pressure to 75 L at 40° C. or lower, and then methanol (37.0 kg) and ethanol (17.3 kg) were added. Methanesulfonic acid (42.7 kg, 444 mol, 8.0 eq.) was added at 10° C. under a nitrogen atmosphere, and it was washed into the mixture with methanol (4.2 kg) and stirred at 40° C. for 28 hours. After confirming completion of the reaction, the mixture was cooled to 20° C., methyl tert-butyl ether (385.8 kg) was added dropwise, and stirring was continued for 1 hour. After cooling to 0° C., the mixture was filtered and rinsed with a liquid mixture of methyl tert-butyl ether and ethanol (methyl tert-butyl ether/ethanol=1.64/0.36 vol., 39.2 kg) and isopropyl acetate (45.5 kg). The obtained crystals were dried under reduced pressure at 50° C. or lower to obtain 22.89 kg of the title compound.

$^1$H NMR Spectrum (DMSO-$d_6$) δ (ppm): 2.32 (3H, s), 2.84 (3H, d, J-4.5 Hz), 3.15 (3H, s), 3.51-3.54 (2H, m), 4.08-4.11 (2H, m), 6.01 (1H, d, J=2.3 Hz), 6.63-6.66 (2H, m), 7.50 (1H, s), 7.61 (2H, br s), 7.79 (1H, d, J=3.8 Hz), 7.90 (1H, d, J=7.2 Hz), 8.10 (1H, s), 8.18 (1H, q, J-4.2 Hz), 12.82 (1H, brs)

Production Example 10-2: Production of 5-(2-aminopyridin-4-yl)oxy)-6-(2-methoxyethoxy)-N-methyl-1H-indole-1-carboxamide methanesulfonate (methanesulfonate of (2i))

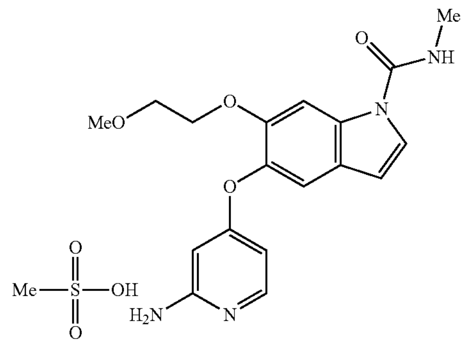

Methanol (33.2 kg) was added to a solution of 6-(2-methoxyethoxy)-N-methyl-5-({2-[(2,4,4-trimethylpentan-2-yl)amino]pyridin-4-yl}oxy)-1H-indole-1-carboxamide (47.8 kg content with previous step as 100%, 102 mol) in ethanol (183 L), under a nitrogen atmosphere. Methanesulfonic acid (117.7 kg, 1225 mol, 12.0 eq.) was added, and it was washed into the mixture with methanol (4.7 kg) and stirred at 25 to 32° C. for 21 hours, after which 5-((2-aminopyridin-4-yl)oxy)-6-(2-methoxyethoxy)-N-methyl-1H-indole-1-carboxamide (46 g) was added. Methyl tert-butyl ether (355.3 kg) was added dropwise to the crystal-precipitated suspension, and the mixture was cooled to 2 to 5° C. The precipitated solid was filtered off and rinsed with a mixture of methyl tert-butyl ether (126.8 kg) and ethanol (54.0 kg), and isopropyl acetate (208.7 kg). The obtained crystals were dried under reduced pressure at 50° C. or lower to obtain 38.04 kg of the title compound.

Production Example 11: Production of 5-((2-amino-pyridin-4-yl)oxy)-6-(2-methoxyethoxy)-N-methyl-1H-indole-1-carboxamide (2i)

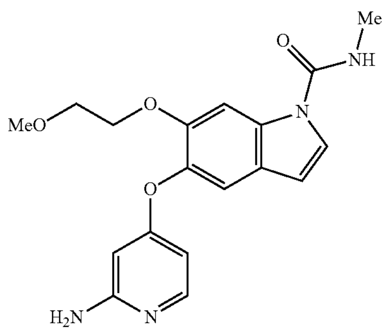 [SMILES: CNC(=O)n1ccc2cc(Oc3ccnc(N)c3)c(OCCOC)cc21]

An aqueous solution of IN sodium hydroxide (2.71 kg caustic soda flake, 67.7 mol, 1.54 eq., 67.7 kg water) was added to a suspension of 5-((2-aminopyridin-4-yl)oxy)-6-(2-methoxyethoxy)-N-methyl-1H-indole-1-carboxamide methanesulfonate (19.9 kg, 44.0 mol) in tetrahydrofuran (159.2 kg) under a nitrogen atmosphere, and the mixture was stirred at 25° C. for 30 minutes. Isopropyl acetate (156.2 kg) was added to the reaction mixture prior to liquid separation, and then the organic layer was rinsed with 5% brine (2.99 kg salt, 56.7 kg water). The obtained organic layer was rinsed with water (59.7 kg) and then clarified by filtration and washed in with isopropyl acetate (8.7 kg). It was subsequently concentrated under reduced pressure to 100 L at 40° C. or lower, and further subjected to azeotropic distillation 4 times with acetonitrile (78.2 kg). Acetonitrile (15.6 kg) was added to the concentrate and the mixture was stirred at 48° C. for 1 hour. The suspension was cooled to 0° C. and then filtered and rinsed with acetonitrile (23.5 kg). The obtained crystals were dried under reduced pressure at 50° C. or lower to obtain 13.91 kg of the title compound.

$^1$H NMR Spectrum (DMSO-$d_6$) δ (ppm): 2.83 (3H, d, J-4.4 Hz), 3.18 (3H, s), 3.50-3.54 (2H, m), 4.04-4.08 (2H, m), 5.69 (1H, d, J=1.8 Hz), 5.76 (2H, s), 6.09 (1H, dd, J-5.7, 2.2 Hz), 6.59 (1H, d, J=3.5 Hz), 7.33 (1H, s), 7.71-7.74 (2H, m), 8.03 (1H, s), 8.10-8.14 (1H, m)

Production Example 11-2: Production of 5-((2-aminopyridin-4-yl)oxy)-6-(2-methoxyethoxy)-N-methyl-1H-indole-1-carboxamide (2i)

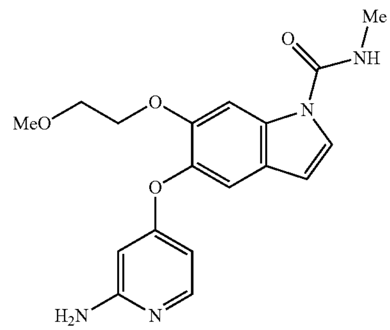 [SMILES: CNC(=O)n1ccc2cc(Oc3ccnc(N)c3)c(OCCOC)cc21]

An aqueous solution of 1 N sodium hydroxide (5.5 kg caustic soda flake, 137.5 mol, 1.70 eq., 138 kg was added water) to a suspension of 5-((2-aminopyridin-4-yl)oxy)-6-(2-methoxyethoxy)-N-methyl-1H-indole-1-carboxamide methanesulfonate (36.6 kg, 80.9 mol) in tetrahydrofuran (292.5 kg) under a nitrogen atmosphere, and the mixture was stirred at 20° C. for 30 minutes. Isopropyl acetate (287 kg) was added to the reaction mixture prior to liquid separation, and then the organic layer was rinsed with 5% brine (5.5 kg salt, 104 kg water). The obtained organic layer was rinsed with water (110 L) and then clarified by filtration and washed in with isopropyl acetate (47.9 kg). It was subsequently concentrated under reduced pressure to 184 L at 40° C. or lower, and further subjected to azeotropic distillation 4 times with acetonitrile (144 kg). Acetonitrile (28.8 kg) was added to the concentrate and the mixture was stirred at 45 to 46° C. for 1 hour. The suspension was cooled to 2° C. and then filtered and rinsed with acetonitrile (43.2 kg). The obtained crystals were dried under reduced pressure at 50° C. or lower to obtain 25.92 kg of the title compound.

The invention claimed is:

1. A process for producing compound (2i):

(2i)

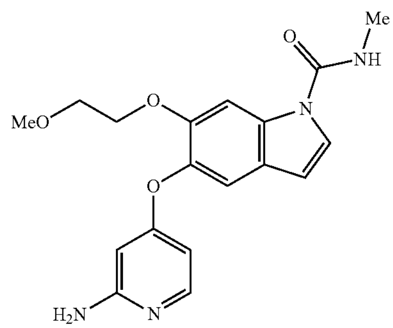

or a salt thereof, wherein the process comprises:

2-a) step 2-a) in which a protecting group is introduced into compound (1g):

(1g)

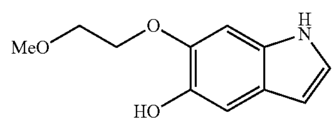

to produce compound (2a):

(2a)

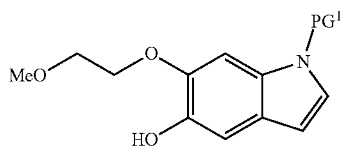

(where $PG^1$ represents a nitrogen protecting group), 2-b) step 2-b) in which compound (2a) obtained in step 2-a) and compound (2b):

(2b)

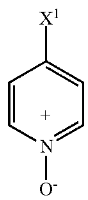

(where $X^1$ represents a leaving group), are reacted in the presence of a base to produce compound (2c):

(2c)

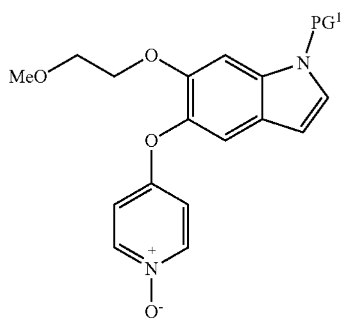

(where $PG^1$ represents the same group as specified above), 2-c) step 2-c) in which compound (2c) obtained in step 2-b) and compound (2d):

$R^1—NH_2$ (2d)

(where $R^1$ represents a tert-pentyl, tert-butyl, tert-octyl or cumyl group), are reacted in the presence of an activating agent to produce compound (2e):

(2e)

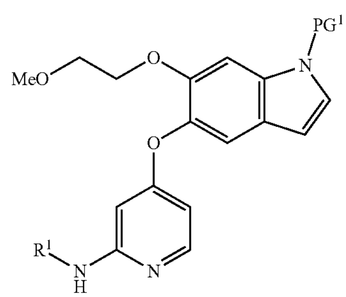

(where $PG^1$ and $R^1$ represent the same groups as specified above), 2-d) step 2-d) in which $PG^1$ in compound (2e) obtained in step 2-c) is removed to produce compound (2f):

(2f)

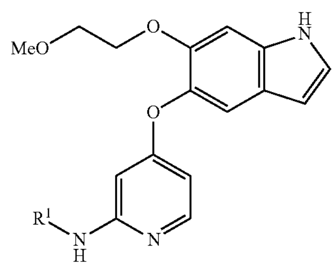

(where $R^1$ represents the same group as specified above), 2-e) step 2-e) in which compound (2f) obtained in step 2-d) and compound (2g-1) or compound (2g-2):

(2g-1)

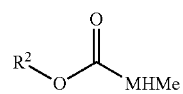

(2g-2)

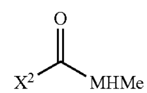

(where $R^2$ of formula (2g-1) is a $C_{1-6}$ alkyl group or $C_{6-10}$ aryl group, the $C_{1-6}$ alkyl group optionally having 1 to 3 identical or different substituents selected from the group consisting of halogen atoms and methoxy groups, and the $C_{6-10}$ aryl group optionally having 1 to 3 identical or different substituents selected from halogen atoms and methyl, methoxy and nitro groups, and $X^2$ of formula (2g-2) represents a halogen atom), are reacted in the presence of a base to produce compound (2h):

(2h)

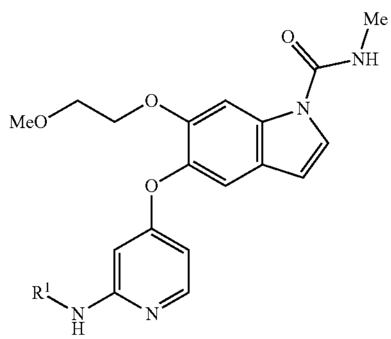

(where $R^1$ represents the same group as specified above), and 2-f) step 2-f) in which $R^1$ of compound (2h) obtained in step 2-e) is removed to produce compound (2i):

(2i)

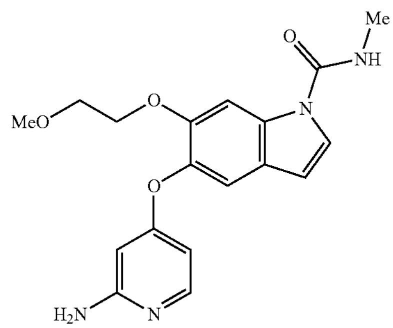

and if necessary step 2-g) in which compound (2i) obtained in step 2-f) is converted to a salt.

2. The production process according to claim 1, wherein compound (2b) is 4-nitropyridin-1-ium-oleate.

3. The production process according to claim 1, wherein compound (2d) is 1,1,3,3-tetramethylbutylamine.

4. The production process according to claim 1, wherein compound (2d) is cumylamine.

5. The production process according to claim 1, wherein the activating agent is p-toluenesulfonyl chloride.

6. A process for producing compound (1g):

(1g)

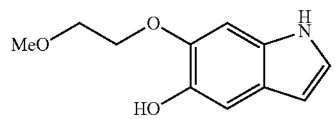

wherein the process comprises:

1-a) step 1-a) in which 1,2-(methylenedioxy)-4-nitrobenzene and 4-bromobenzyl alcohol are reacted in the presence of a base to produce compound (1c):

(1c)

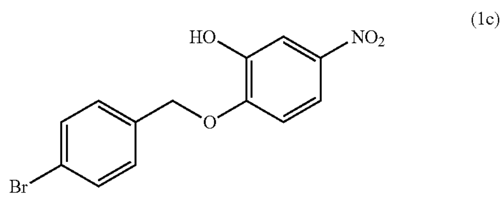 [SMILES: O=[N+]([O-])c1ccc(OCc2ccc(Br)cc2)c(O)c1]

1-b) step 1-b) in which compound (1c) obtained in step 1-a) and a methoxyethylating agent are reacted in the presence of a base to produce compound (1d):

(1d)

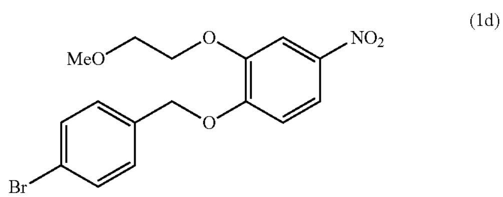 [SMILES: COCCOc1cc([N+](=O)[O-])ccc1OCc1ccc(Br)cc1]

1-c) step 1-c) in which compound (1d) obtained in step 1-b) and a cyanomethylating agent are reacted in the presence of a base to produce compound (1f):

(1f)

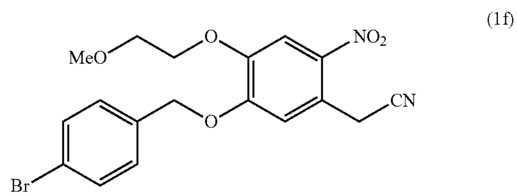 [SMILES: COCCOc1cc([N+](=O)[O-])c(CC#N)cc1OCc1ccc(Br)cc1]

and 1-d) step 1-d) in which compound (1g):

(1g)

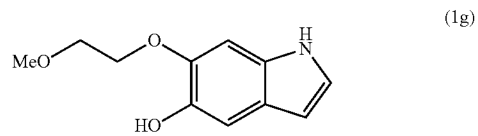 [SMILES: COCCOc1cc2[nH]ccc2cc1O]

is produced by conversion of the nitro group of compound (11) obtained in step 1-c) to an amino group, removal of the 4-bromobenzyl group, and ring closure with an acid catalyst.

7. The production process according to claim 6, wherein a palladium catalyst and sulfuric acid are used in step 1-d).

* * * * *